(12) United States Patent
Woster et al.

(10) Patent No.: US 9,186,391 B2
(45) Date of Patent: Nov. 17, 2015

(54) CYCLIC PEPTIDE INHIBITORS OF LYSINE-SPECIFIC DEMETHYLASE 1

(71) Applicant: MUSC FOUNDATION FOR RESEARCH DEVELOPMENT, Charleston, SC (US)

(72) Inventors: Patrick M. Woster, Charleston, SC (US); Isuru R. Kumarasinghe, Charleston, SC (US)

(73) Assignee: MUSC Foundation for Research Development, Charleston, SC (US)

( * ) Notice: Subject to any disclaimer, the term of this patent is extended or adjusted under 35 U.S.C. 154(b) by 0 days.

(21) Appl. No.: 14/473,305

(22) Filed: Aug. 29, 2014

(65) Prior Publication Data

US 2015/0065434 A1  Mar. 5, 2015

Related U.S. Application Data

(60) Provisional application No. 61/871,688, filed on Aug. 29, 2013.

(51) Int. Cl.
*A61K 38/17* (2006.01)

(52) U.S. Cl.
CPC .................................. *A61K 38/1709* (2013.01)

(58) Field of Classification Search
None
See application file for complete search history.

(56) References Cited

FOREIGN PATENT DOCUMENTS

WO  WO 2010/084160  7/2010
WO  WO 2011/035941  3/2011

OTHER PUBLICATIONS

Wermuth et al Glossary of Terms used in Medicinal Chemistry, Pure and Appl. Chem., vol. 70, No. 5, pp. 1129-1143, (1998).*
Culhane et al., "A mechanism-based inactivator for histone demethylase LSD1," *J. Am. Chem. Soc.*, 128:4536-4537, 2006.
Culhane et al., "Comparative analysis of small molecules and histone substrate analogues as LSD1 lysine demethylase inhibitors," *J. Am. Chem. Soc.*, 132:3164-3176, 2010.
Forneris et al., "A highly specific mechanism of histone H3-K4 recognition by histone demethylase LSD1," *J. Biol. Chem.*, 281:35289-35295, 2006.
Forneris et al., "Human histone demethylase LSD1 reads the histone code," *J. Biol. Chem.*, 280:41360-41365, 2005.
Forneris et al., "Structural basis of LSD1-CoREST selectivity in histone H3 recognition," *J. Biol. Chem.*, 282:20070-20074, 2007.
Hayami et al., "Overexpression of LSD1 contributes to human carcinogenesis through chromatin regulation in various cancers," *Int. J. Cancer*, 128:574-586, 2011.
Hazeldine et al., "Low molecular weight amidoximes that act as potent inhibitors of lysine-specific demethylase 1," *J. Med. Chem.*, 55:7378-7391, 2012.

Hruby, "Designing peptide receptor agonists and antagonists," *Nat. Rev. Drug Discov.*, 1:847-858, 2002.
Huang et al., "Inhibition of lysine-specific demethylase 1 by polyamine analogues results in reexpression of aberrantly silenced genes," *PNAS*, 104:8023-8028, 2007.
Jenuwein and Allis, "Translating the histone code," *Science*, 293:1074-1080, 2001.
Kumarasinghe and Woster, "Synthesis and evaluation of novel cyclic peptide inhibitors of lysine-specific demethylase 1," *ACA Med. Chem. Lett.*, 5:29-33, 2014.
Kutz et al., "3,5-Diamino-1,2,4-triazoles as a novel scaffold for potent, reversible LSD1 (KDM1A) inhibitors," *Med. Chem. Commun.*, First published online Aug. 22, 2014.
Latham and Dent, "Cross-regulation of histone modifications," *Nat. Struct. Mol. Biol.*, 14:1017-1024, 2007.
Lim et al., "Lysine-specific demethylase 1 (LSD1) is highly expressed in ER-negative breast cancers and a biomarker predicting aggressive biology," *Carcinogenesis*, 31:512-520, 2010.
Ogasawara et al., "Lysine-specific demethylase 1-selective inactivators: protein-targeted drug delivery mechanism," *Angew Chem. Int. Ed. Engl.*, 52:8620-8624, 2013.
Radisky and Radisky, "Stromal induction of breast cancer: inflammation and invasion," *Reviews in Endocrine & Metabolic Disorders*, 8:279-287, 2007.
Radisky et al., "Fibrosis and cancer: do myofibroblasts come also from epithelial cells via EMT?," *J. Cell Biochem.*, 101:830-839, 2007.
Rotili and Mai, "Targeting Histone Demethylases: A New Avenue for the Fight against Cancer," *Genes Cancer*, 2:663-679, 2011.
Rybinski et al., "The wound healing, chronic fibrosis, and cancer progression triad," *Physiological Genomics*, 46:223-244, 2014.
Schmitt et al., "Nonpeptidic propargylamines as inhibitors of lysine specific demethylase 1 (LSD1) with cellular activity," *J. Med. Chem.*, 56:7334-7342, 2013.
Schulte et al., "Lysine-specific demethylase 1 is strongly expressed in poorly differentiated neuroblastoma: implications for therapy," *Cancer Res.*, 69:2065-2071, 2009.
Sharma et al., "(Bis) urea and (bis)thiourea inhibitors of lysine-specific demethylase 1 as epigenetic modulators," *J. Med. Chem.*, 53:5197-5212, 2010.
Sharma et al., "Polyamine-based small molecule epigenetic modulators," *Med. Chem. Comm.*, 3:14-21, 2012.
Shi et al., "Histone demethylation mediated by the nuclear amine oxidase homolog LSD1," *Cell*, 119:941-953, 2004.
Shi, "Histone lysine demethylases: emerging roles in development, physiology and disease," *Nat. Rev. Genet.*, 8:829-833, 2007.
Stavropoulos and Hoelz, "Lysine-specific demethylase 1 as a potential therapeutic target," *Expert Opin. Ther. Targets*, 11:809-820, 2007.
Strahl and Allis, "The language of covalent histone modifications," *Nature*, 403:41-45, 2000.
Suzuki and Miyata, "Lysine demethylases inhibitors," *Journal of Medicinal Chemistry*, 54:8236-8250, 2011.
Szewczuk et al., "Mechanistic analysis of a suicide inactivator of histone demethylase LSD1," *Biochemistry*, 46:6892-6902, 2007.
Yang et al., "Structural basis of histone demethylation by LSD1 revealed by suicide inactivation," *Nat. Struct. Mol. Biol.*, 14:535-539, 2007.
Zheng et al., "Triazole-dithiocarbamate based selective lysine specific demethylase 1 (LSD1) inactivators inhibit gastric cancer cell growth, invasion, and migration," *J. Med. Chem.*, 56(21):8543-8560, 2013.

* cited by examiner

*Primary Examiner* — Thomas S Heard
(74) *Attorney, Agent, or Firm* — Parker Highander PLLC

(57) ABSTRACT

Provided herein are cyclic peptide inhibitors of lysine-specific demethylase 1. These cyclic peptides have the potential to treat cancer, diabetes, cardiovascular disease, and neurological disorders.

10 Claims, 10 Drawing Sheets
(4 of 10 Drawing Sheet(s) Filed in Color)

1
$K_I$ (LSD1) = 5 nM

2
$K_I$ (LSD1) = 9 nM

3

N-methylpropargyl-K4H3(1-21), 4
$K_I$ (LSD1) = 107 nM hydrazino-K4H3(1-21), 5
$K_I$ (LSD1) = 4.35 nM 6
30% inhibition at 10 µM

7
$IC_{50}$ 2.1 µM

8
$K_I$ (LSD1) = 0.04 µM

SEQUENCE LISTING

<160> NUMBER OF SEQ ID NOS: 8

<210> SEQ ID NO 1
<211> LENGTH: 21
<212> TYPE: PRT
<213> ORGANISM: Artificial Sequence
<220> FEATURE:
<223> OTHER INFORMATION: Synthetic peptide

<400> SEQUENCE: 1

Ala Arg Thr Met Gln Thr Ala Arg Lys Ser Thr Gly Gly Lys Ala Pro
1               5                   10                  15

Arg Lys Gln Leu Ala
            20

<210> SEQ ID NO 2
<211> LENGTH: 21
<212> TYPE: PRT
<213> ORGANISM: Artificial Sequence
<220> FEATURE:
<223> OTHER INFORMATION: Synthetic peptide

<400> SEQUENCE: 2

Ala Lys Thr Met Gln Thr Ala Arg Lys Ser Thr Gly Gly Glu Ala Pro
1               5                   10                  15

Arg Lys Gln Leu Ala
            20

<210> SEQ ID NO 3
<211> LENGTH: 21
<212> TYPE: PRT
<213> ORGANISM: Artificial Sequence
<220> FEATURE:
<223> OTHER INFORMATION: Synthetic peptide

<400> SEQUENCE: 3

Ala Arg Thr Met Lys Thr Ala Arg Lys Glu Thr Gly Gly Lys Ala Pro
1               5                   10                  15

Arg Lys Gln Leu Ala
            20

<210> SEQ ID NO 4
<211> LENGTH: 21
<212> TYPE: PRT
<213> ORGANISM: Artificial Sequence
<220> FEATURE:
<223> OTHER INFORMATION: Synthetic peptide

<400> SEQUENCE: 4

Ala Lys Thr Met Gln Thr Ala Arg Lys Glu Thr Gly Gly Lys Ala Pro
1               5                   10                  15

Arg Lys Gln Leu Ala
            20

<210> SEQ ID NO 5
<211> LENGTH: 21
<212> TYPE: PRT
<213> ORGANISM: Artificial Sequence
<220> FEATURE:
<223> OTHER INFORMATION: Synthetic peptide

<400> SEQUENCE: 5

Ala Lys Thr Met Gln Thr Ala Arg Lys Ser Thr Glu Gly Lys Ala Pro
1               5                   10                  15

Arg Lys Gln Leu Ala
            20

<210> SEQ ID NO 6
<211> LENGTH: 21
<212> TYPE: PRT
<213> ORGANISM: Artificial Sequence
<220> FEATURE:
<223> OTHER INFORMATION: Synthetic peptide

<400> SEQUENCE: 6

Ala Lys Thr Met Glu Thr Ala Arg Lys Ser Thr Gly Gly Lys Ala Pro
1               5                   10                  15

Arg Lys Gln Leu Ala
            20

```
<210> SEQ ID NO 7
<211> LENGTH: 21
<212> TYPE: PRT
<213> ORGANISM: Artificial Sequence
<220> FEATURE:
<223> OTHER INFORMATION: Synthetic peptide

<400> SEQUENCE: 7

Ala Arg Thr Met Gln Thr Ala Arg Lys Ser Thr Gly Gly Glu Ala Pro
1               5                   10                  15

Arg Lys Gln Leu Ala
            20

<210> SEQ ID NO 8
<211> LENGTH: 21
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(21)
<223> OTHER INFORMATION: X is any amino acid

<400> SEQUENCE: 8

Ala Xaa Thr Met Xaa Thr Ala Arg Lys Xaa Thr Xaa Gly Xaa Ala Pro
1               5                   10                  15

Arg Lys Gln Leu Ala
            20
```

CYCLIC PEPTIDE INHIBITORS OF LYSINE-SPECIFIC DEMETHYLASE 1

This invention was made with government support under Grant No. R01 CA149095 awarded by the National Institutes of Health. The government has certain rights in the invention.

BACKGROUND OF THE INVENTION

The present application claims the priority benefit of U.S. provisional application No. 61/871,688, filed Aug. 29, 2013, the entire contents of which are incorporated herein by reference.

The sequence listing that is contained in the file named "MESCP0078US_ST25.txt", which is 3 KB (as measured in Microsoft Windows®) and was created on Aug. 22, 2014, is filed herewith by electronic submission and is incorporated by reference herein.

1. Field of the Invention

The present invention relates generally to the field of medicine. More particularly, it concerns cyclic peptide inhibitors of lysine-specific demethylase 1 (LSD1).

2. Description of Related Art

Lysine-rich histone tails protrude through nucleosomal DNA strands, and act as sites for several post-translational modifications (PTMs), allowing alteration of higher order chromatin structure. There are numerous lysine methylation sites on histone tails, and PTMs at specific lysine marks can promote transcriptional activation or silencing. The flavin-dependent lysine-specific demethylase 1 (LSD1) selectively removes methyl groups from mono- and di-methylated histone 3 lysine 4 (1-13K4), resulting in gene silencing. More specifically, LSD1 binds to the co-repressor protein CoREST and catalyzes the oxidative demethylation of histone 3 methyllysine 4 (H3K4me1) and histone 3 dimethyllysine 4 (H3K4me2). Methylated histone 3 lysine 4 (H3K4) is a transcription-activating chromatin mark at gene promoters, and demethylation of this mark by LSD1 is known to aberrantly silence expression of tumor suppressor genes important in human cancer. Because it is overexpressed in many human cancers. LSD 1 has emerged as an important target for the development of specific inhibitors as a new class of antitumor agents.

To date a handful of small molecule inhibitors of LSD1 have been described. Effective LSD1 inhibitors include tranylcypromine-based analogues, such as 1 and 2 (WO2010/084160; WO2011/035941), oligoamines such as verlindamycin (aka 2d) 3 (Huang et al., 2007) and related isosteric ureas and thioureas (Sharma et al., 2010; Sharma et al, 2012), and peptide based LSD1 inhibitors 4 and S (Cuthane et al., 2006; Culhane et al., 2010; Szewczuk et al., 2007; Yang et al., 2007). Fomeris et al. (2007) described a 21 amino acid peptide analogous to the histone 3 lysine tail, wherein Lys4 is replaced by a methionine compound 8, FIG. 1). Although this linear peptide is a potent inhibitor of LSD1/CoREST ($K_i$ 0.04 μM), it has little potential for use as a drug, since it would be poorly transported across membranes, and would be rapidly hydrolyzed in viva. Cyclic peptides are more stable against proteolytic enzymes than their linear counterparts (Hruby et al., 2002), and can facilitate elucidation of bioactive conformations that are important for biological activity. To date, a cyclic peptide inhibitor of LSD1 has not been described.

SUMMARY OF THE INVENTION

The present invention provides cyclic peptide inhibitors of LSD1. In one embodiment, cyclic peptide lysine-specific demethylase 1 (LSD1) inhibitor is provided that comprises a sequence at least 90% identical to the peptide sequence of SEQ ID NO: 1. In some aspects, the cyclic peptide inhibitor may be at least 95% identical to the sequence provided in SEQ ID NO: 1. In one aspect, the cyclic peptide may comprise a lactam bridge. Thus, the peptides of the present embodiments may be cyclized via the formation of a lactam bridge between, for example, a Lys and a Glu amino acid side chain. In one aspect, the cyclic peptide may be a stapled peptide. Thus, the peptides of the present embodiments may be cyclized via the formation of an all-hydrocarbon "staple."

In one aspect, the second amino acid of the peptide is a Lys substitution, the fourteenth amino acid is a Glu substitution, and the lactam bridge is formed between Lys2 and Glu14. In this aspect, the sequence of the peptide is the sequence provided in SEQ ID NO: 2.

In another aspect, the fifth amino acid of the peptide is a Lys substitution, the tenth is a Glu substitution, and the lactam bridge is formed between Lys5 and Glu10. In this aspect, the sequence of the peptide is the sequence provided in SEQ ID NO: 3.

In another aspect, the second amino acid of the peptide is a Lys substitution, the tenth is a Glu substitution, and the lactam bridge is formed between Lys2 and Glu10. In this aspect, the sequence of the peptide is the sequence provided in SEQ ID NO: 4.

In another aspect, the second amino acid of the peptide is a Lys substitution, the twelfth is a Glu substitution, and the lactam bridge is formed between Lys2 and Glu12. In this aspect, the sequence of the peptide is the sequence provided in SEQ ID NO: 5.

In another aspect, the second amino acid of the peptide is a Lys substitution, the fifth is a Glu substitution, and the lactam bridge is formed between Lys2 and Glu5. In this aspect, the sequence of the peptide is the sequence provided in SEQ ID NO: 6.

In yet another aspect, the fourteenth amino acid of the peptide is a Gilt substitution and the lactam bridge is formed between Lys9 and Glu14. In this aspect, the sequence of the peptide is the sequence provided in SEQ ID NO: 7.

In one embodiment, the cyclic peptide LSD1 inhibitors of the present invention comprise the sequence of H-AX$_1$TMX$_2$TARKX$_3$TX$_4$GX$_5$APRKQLA-NH$_2$ (SEQ ID NO: 8), wherein X$_1$ is K or R; X$_2$ is Q, K, or E; X$_3$ is S or E; X$_4$ is G or E; and X$_5$ is K or E. In one aspect, X$_1$ is K, X$_2$ is Q, X$_3$ is S, X$_4$ is G, and X$_5$ is E, and a lactam bridge is formed between X$_1$ and X$_5$. In one aspect, X$_1$ is K, X$_2$ is Q, X$_3$ is E, X$_4$ is G, and X$_5$ is K, and a lactam bridge is formed between X$_1$ and X$_3$. In one aspect, X$_1$ is K, X$_2$ is Q, X$_3$ is S, X$_4$ is E, and X$_5$ is K, and a lactam bridge is formed between X$_1$ and X$_4$. In one aspect, X$_1$ is K, X$_2$ is E, X$_3$ is S, X$_4$ is G, and X$_5$ is K, and a lactam bridge is formed between X$_1$ and X$_2$. In one aspect, X$_1$ is R, X$_2$ is K, X$_3$ is E, X$_4$ is G, and X$_5$ is K, and a lactam bridge is formed between X$_2$ and X$_3$. In one aspect, X$_1$ is R, X$_2$ is Q, X$_3$ is S, X$_4$ is G, and X$_5$ is E, and a lactam bridge is formed between Lys9 and X$_5$.

In various aspects, a cyclic peptide of the invention may comprise L or D amino acids. In various aspects, a cyclic peptide of the invention may comprise a mix of L and D amino acids. In some aspects, a cyclic peptide of the invention may comprise N-methylated amino acids. In some aspects, a cyclic peptide of the invention may comprise β-amino acids. In some aspects, a cyclic peptide of the invention may be, partially or fully, a peptidomimetic or peptoid. In some aspects, a cyclic peptide of the invention may be lipidated and/or PEG-ylated.

In one embodiment, the present invention provides a pharmaceutical formulation comprising a cyclic peptide of the embodiments. The cyclic peptide LSD1 inhibitor may be in a pharmaceutically acceptable carrier. In some aspects, the cyclic peptide may be encapsulated or embedded in a delivery vehicle. In various aspects, the delivery vehicle is a liposome, a lysosome, a microcapsule, or a nanoparticle.

In one embodiment, the present invention provides a method of treating a tumor cell or a subject having a tumor cell comprising administering to the tumor cell or the subject a pharmaceutical formulation comprising a cyclic peptide LSID1 inhibitor of the embodiments. In various aspects, treating may comprise inhibiting cancer cell growth, inhibiting cancer cell proliferation, and/or reducing tumor burden. In one aspect, the subject may have been identified as having a lysine-specific demethylase 1-overexpressing tumor. In one aspect, the subject may be a human subject.

In one aspect, the tumor cell may be a cell of breast cancer, prostate cancer, ovarian cancer, pancreatic cancer, colon cancer, melanoma, neuroblastoma, or lung cancer. In one aspect, the pharmaceutical formulation may be administered intravenously, intradermally, intraarterially, intraperitoneally, intralesionally, intracranially, intraarticularly, intraprostaticaly, intrapleurally, intratracheally, intraocularly, intranasally, intravitreally, intravaginally, intrarectally, intramuscularly, subcutaneously, subconjunctival, intravesicularly, mucosally, intrapericardially, intraumbilically, orally, by inhalation, by injection, by infusion, by continuous infusion, by localized perfusion bathing target cells directly, via a catheter, or via a lavage.

In some aspect, the method may further comprise administering to the tumor cell or the subject a second anti-cancer agent. Said second anti-cancer agent may be administered prior to, after, and/or at the same time as the peptide. In some aspects, the peptide may be administered at a dose of 0.1-500 mg/kg/d, More preferably, the peptide may be administered at a dose of 10-100 mg/kg/d.

In certain aspects, the peptide may be administered daily. Said daily administration may continue for 7 days, 2 weeks, 3 weeks, 4 weeks, one month, 6 weeks, 8 weeks, two months, 12 weeks, or 3 months, or more. In certain aspects, the peptide may be administered weekly. Said weekly administration may continue for 2 weeks, 3 weeks, 4 weeks, 6 weeks, 8 weeks. 10 weeks, or 12 weeks, or more.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1:
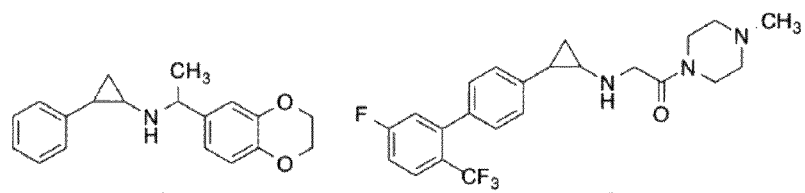
FIG. 1—Synthetic inhibitors of LSD1.
Figure 1:
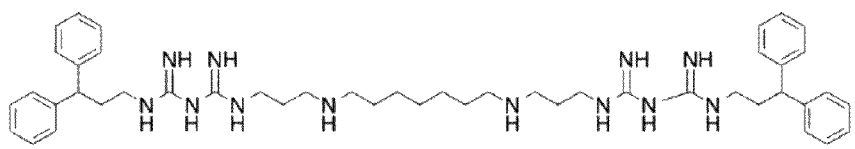
Figure 1:
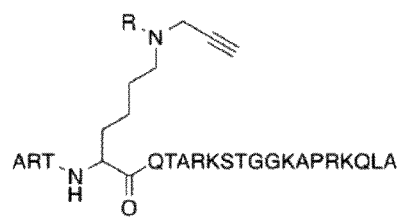
Figure 1:
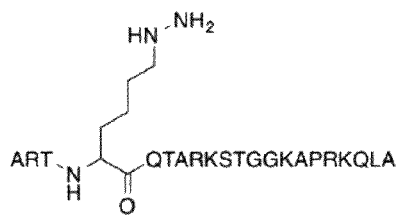
Figure 1:
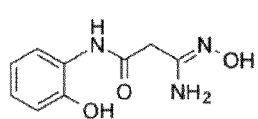
Figure 1:
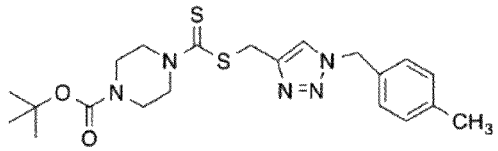
Figure 1:
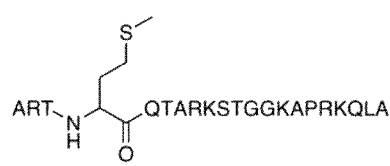

Rationally designed cyclic peptides may act as potent inhibitors of histone demethylation catalyzed by LSD1, and may be used as effective antitumor agents in vivo alone or when lipidated. Thus, provided herein is a series of cyclic LSD1 inhibitory peptides is described. For example, a cyclic peptide LSD1 inhibitor ($IC_{50}$ 2.1 μM; Ki 385 nM) is provided that is significantly more stable to hydrolysis in rat plasma than its corresponding linear analogue. Peptidomimetic and peptoid residues will be systematically substituted into the cyclic structure of the cyclic peptides provided herein to enhance enzyme inhibitory activity, improve cell penetration and increase stability. Inhibitors may be lipidated to enhance delivery, confer oral activity, and/or create the potential for selective targeting tumor cells, In vivo efficacy of the cyclic peptides will be determined in a murine xenograph model of tumor growth. The resulting cyclic peptide inhibitors of a histone demethylase-1 enzyme will be highly specific and potentially be superior to existing agents in potency and off-target effects.

Provided herein is a series of cyclic and linear peptides that are effective inhibitors of LSD1. Linear peptide 9 and cyclic peptide 11 inhibit LSD1 in vitro by 91% and 94%, respectively, at a concentration of 10 µM. In addition, 11 possesses an $IC_{50}$ value of 2.1 µM against recombinant human LSD1. In addition to being potent inhibitors of LSD1, the cyclic peptide analogues have greater stability against proteolytic degradation than their linear homologues. As LSD1 inhibitors, these cyclic peptides have the potential to act as epigenetic modulators. Aberrant gene silencing not only plays a role in cancer, but also in other diseases such as diabetes, cardiovascular disease, and neurological disorders. Epigenetic modulators can be used to reverse aberrant gene silencing, and thus have a positive effect on disease progression.

I. Epigenetic Regulation and LSD1 Inhibitors

Histone proteins occur as octamers that consist of one H3-H4 tetramer and two H2A-H2B dimers (Strata and Allis, 2000; Arrowsmith et al., 2012). These proteins interact with double stranded DNA such that approximately 146 base pairs of DNA wrap around a histone octamer to form a nucleosome. The lysine-rich tails of histones, consisting of up to 40 amino acid residues, protrude through the nucleosotnal DNA strand and act as a site for post-translational modification of chromatin (acetylation, methylation, phosphorylation, ubiquitylation, sumoylation, ADP ribosylation, deamination and proline isomerization), allowing alteration of higher order nucleosome structure (Jenuwein and Allis, 2001; Latham and Dent, 2007). There are numerous lysine methylation sites on histone tails, and post-translational modifications at specific methylation marks can promote transcriptional activation or silencing.

In cancer, the most important PTMs are mediated by epigenetic writers including protein arginine methyltransferases (PRMTs), lysine methyltransferases (KMTs) and histone acetyltransferases (HATS), and by epigenetic erasers including 2 groups of histone demethylases (KDM1 and KDM2) and the 11 zinc-dependent histone deacetylases (HDACs). Epigenetic marks that undergo PTMs are read by epigenetic reader proteins, and the resulting complex signals up or down regulation of gene expression. The flavin-dependent histone demethylase LSD1 (also known as BHC110 and KDM1A) (Shi, et al., 2007; Shi et al., 2004) bound to the CoREST corepressor, catalyzes the oxidative demethylation of histone 3 methyllysine 4 (H3K4me1) and histone 3 dimethyllysine 4 (H3K4me2). LSD1 can also demethylate histone 3 lysine 9 (H3K9) when it is associated with the androgen receptor.8 Methylated histone 3 lysine 4 (H3K4) is a transcription activating mark at gene promoters, and aberrant demethylation of this mark by LSD1. is known to silence expression of tumor suppressor genes important in human cancer (Huang et al., 2007). By contrast, H3K9 methylation promotes transcriptional repression, and demethylation enhances gene expression (Forneris et al., 2005). More broadly, LSD1 is known to modulate activation or repression of a number of important genes (Suzuki and Miyata, 2011). Because it is overexpressed in a number of human cancers (neuroblastoma, retinoblastoma, prostate cancer, breast cancer, lung cancer and bladder cancer) (Hayami et al., 2011; Lim et al., 2010; Schulte et al., 2009; Rotili et al., 2011), LSD1 has emerged as an target for the development of specific inhibitors as a new class of antitumor drugs (Stavropoulos and Hoelz, 2007).

To date a number of small molecule inhibitors of LSD1 have been described, as shown in FIG. 1. Effective LSD1 inhibitors include tranylcypromine-based analogues, such as 1 and 2 (WO2010/084160; WO2011/035941), oligoaraines such as verlindamycin 3 and related isosteric ureas and thioureas (Huang et al., 2007; Sharma et al., 2010; Sharma et al., 2012) and peptide based LSD1 inhibitors such as 4 and 5 (Cuthane et al., 2006; Cullhane et al., 2010; Szewdzuk et al., 2007; Yang et al., 2007; Ogasawara et al., 2013). Small molecule inhibitors identified by screening include amidoximes such as 6 (Hazeldine et al., 2012) and triazole-dithiocarbamates such as 7 (Zheng et al., 2013). Many of the more potent LSD1 inhibitors are based on a tranylcypromine scaffold; however, this structural motif raises the possibility of off-target effects mediated by MAO or other flavin-dependent amine oxidases. In addition, it has not been established what potency is required in an LSD1 inhibitor to produce a beneficial epigenetic effect when used in combination with existing antitumor agents such as 5-azacytidine (5-AC). Significant increases in H3K4 methylation and re-expression of tumor suppressor proteins have been observed at concentrations well below the LSD1 $IC_{50}$ and cellular $GI_{50}$ values, thus suggesting the use of selectivity and epigenetic biomarkers as end points rather than cytotoxicity. Non-cytotoxic LSD 1 inhibitors are potentially useful in cancer combination therapy, and, without being bound by theory, because inflammation and the chronic fibrosis microenvironment are linked to tumorigenesis through epigenetic factors (Radisky et al., 2007; Radisky and Radisky, 2007; Rybinski et al., 2014), such compounds may be chemoprevention agents.

Figure 2:
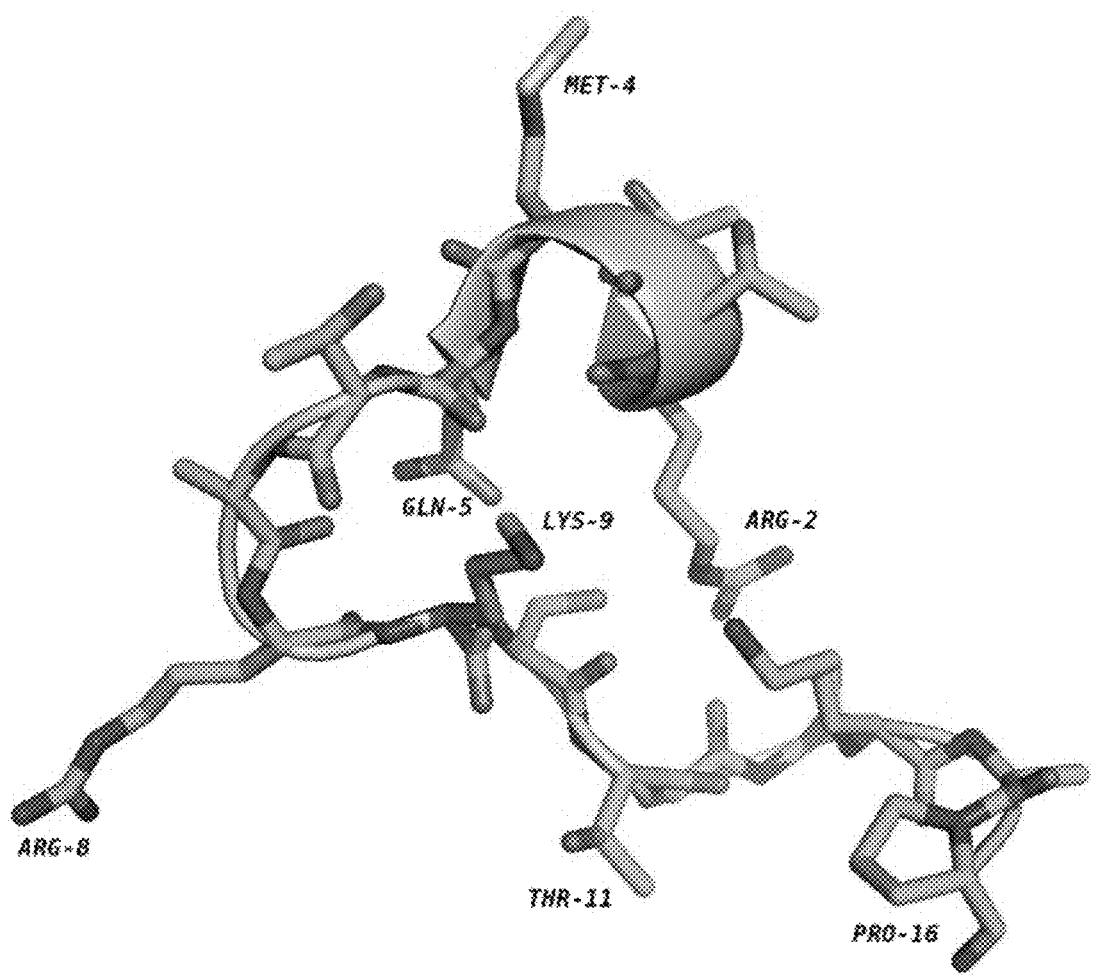
FIG. 2—X-ray crystallographic conformation reported for 6 bound to LSD1. The primary sequence of 6 is ARTM-QTARKSTGGKA-PRKQLA (SEQ ID NO: 1) (Fomeris et al., 2007). Amino acid residues 1-16, which have well defined secondary structure, are shown; residues 17-21 occur as random coils and are not shown.

Forneris et al. (2007) described a 21-amino acid peptide 8 (FIG. 2) that is analogous to the H3 histone tail, wherein Lys4 was replaced by a methionine. This linear peptide is a potent inhibitor of recombinant LSD1 bound to CoREST ($K_i$ 0.05 µM) (Forneris et al., 2007; Culhane et al., 2010). X-ray crystallography indicates that peptide 8 bound in the LSD1 active site adopts a folded conformation with three structural elements (FIG. 2): a helical turn (residues 1-5) that positions Met4 near the FAD cofactor, a sharp bend (residues 6-9), and a solvent-exposed linear segment near the edge of the catalytic site (residues 10-16). Residues 17-21 exist as a random coil. Three amino acids, Arg2, Gln5 and Ser10, form the core binding triad in 8 and participate in key intramolecular interactions with LSD1. As shown in FIG. 2, the orientation of 8 in the active site approximates a cyclic peptide structure.

II. Proteins and Peptides

In certain embodiments, the present invention concerns novel compositions comprising at least one protein or peptide, such as a cyclic peptide LSD1 inhibitor.

As used herein, a protein or peptide generally refers, but is not limited to, a protein of greater than about 200 amino acids, up to a full length sequence translated from a gene; a polypeptide of greater than about 100 amino acids; and/or a peptide of from about 3 to about 100 amino acids. For convenience, the terms "protein," "polypeptide" and "peptide are used interchangeably herein.

In certain embodiments the size of at least one protein or peptide may comprise, but is not limited to, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, about 110, about 120, about 130, about 140, about 150, about 160, about 170, about 180, about 190, about 200, about 210, about 220, about 230, about 240, about 250, about 275, about 300, about 325, about 350, about 375, about 400, about 425, about 450, about 475, about 500, about 525, about 550, about 575, about 600, about 625, about 650, about 675, about 700, about 725, about 750, about 775, about 800, about 825, about 850, about 875, about 900, about 925, about 950, about 975, about 1000, about 1100, about 1200, about 1300, about 1400, about 1500, about 1750, about 2000, about 2250, about 2500 or greater amino acid residues.

As used herein, an "amino acid residue" refers to any naturally occurring amino acid, any amino acid derivative or any amino acid mimic known in the art. In certain embodiments, the residues of the protein or peptide are sequential, without any non-amino acids interrupting the sequence of amino acid residues. In other embodiments, the sequence may comprise one or more non-amino acid moieties. In particular embodiments, the sequence of residues of the protein or peptide may be interrupted by one or more non-amino acid moieties.

Accordingly, the term "protein or peptide" encompasses amino acid sequences comprising at least one of the 20 common amino acids found in naturally occurring proteins, or at least one modified or unusual amino acid, including but not limited to those shown in Table 1 below.

TABLE 1

Modified and Unusual Amino Acids

| Abbr. | Amino Acid | Abbr. | Amino Acid |
|---|---|---|---|
| Aad | 2-Aminoadipic acid | EtAsn | N-Ethylasparagine |
| Baad | 3-Aminoadipic acid | Hyl | Hydroxylysine |
| Bala | β-alanine, β-Amino-propionic acid | AHyl | allo-Hydroxylysine |
| Abu | 2-Aminobutyric acid | 3Hyp | 3-Hydroxyproline |
| 4Abu | 4-Aminobutyric acid, piperidinic acid | 4Hyp | 4-Hydroxyproline |
| Acp | 6-Aminocaproic acid | Ide | Isodesmosine |
| Ahe | 2-Aminoheptanoic acid | AIle | allo-Isoleucine |
| Aib | 2-Aminoisobutyric acid | MeGly | N-Methylglycine, sarcosine |
| Baib | 3-Aminoisobutyric acid | MeIle | N-Methylisoleucine |
| Apm | 2-Aminopimelic acid | MeLys | 6-N-Methyllysine |
| Dbu | 2,4-Diaminobutyric acid | MeVal | N-Methylvaline |
| Des | Desmosine | Nva | Norvaline |
| Dpm | 2,2'-Diaminopimelic acid | Nle | Norleucine |
| Dpr | 2,3-Diaminopropionic acid | Orn | Ornithine |
| EtGly | N-Ethylglycine | | |

Proteins or peptides may be made by any technique known to those of skill in the art, including the expression of proteins, polypeptides or peptides through standard molecular biological techniques, the isolation of proteins or peptides from natural sources, or the chemical synthesis of proteins or peptides. The nucleotide and protein, polypeptide and peptide sequences corresponding to various genes have been previously disclosed, and may be found at computerized databases known to those of ordinary skill in the art. One such database is the National Center for Biotechnology Information's Genbank and GenPept databases (available on the world wide web at ncbi.nlm.nih.gov/). Alternatively, various commercial preparations of proteins, polypeptides and peptides are known to those of skill in the art.

Substitution or replacement variants typically contain the exchange of one amino acid for another at one or more sites within the protein or peptide and may be designed to modulate one or more properties of the polypeptide, particularly its effector functions and/or bioavailability. Substitutions may or may not be conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine, or methionine; serine to threonine; threonine to serine; tryptophan to tyrosine; tyrosine to tryptophan or phenylalanine; and valine to isoleucine or leucine.

In addition to a deletion or substitution, a modified protein or peptide may possess an insertion of residues, which typically involves the addition of at least one residue in the protein or peptide. This may include the insertion of a targeting peptide or polypeptide or simply a single residue.

A. Peptoids and Peptidomimetics

A peptidomimetic is a small protein-like chain designed to mimic a peptide. They typically arise either from modification of an existing peptide, or by designing similar systems that mimic peptides, such as peptoids and β-peptides. Irrespective of the approach, the altered chemical structure is designed to advantageously adjust the molecular properties such as, stability or biological activity. This can have a role in the development of drug-like compounds from existing peptides. These modifications involve changes to the peptide that will not occur naturally (such as altered backbones and the incorporation of non-natural amino acids).

Peptoids are oligomers of N-substituted glycines. Despite the structural similarity between peptides and peptoids, peptoids are quite different from peptides in several important ways. First, they are resistant to natural proteases. This is the case because in peptoids, as compared to peptides, the side chain (R group) resides on the nitrogen rather than the chiral carbon atoms. This modification, which displays the peptoid R group in a planar presentation, produces a misalignment of the side chains and the carbonyl groups such that the susceptible (amide) bond is out of range of the nucleophilic catalysts at protease active sites, and hence, not cleavable, Secondly, peptoids are far easier to synthesize than peptides, at least with respect to making compounds with non-natural side chains. The L-amino acids that make up peptides are chiral (optically active) molecules. If non-natural amino acids are to be incorporated into peptides, one must carry out sometimes difficult and expensive syntheses of these building blocks. Peptoids lack chiral centers since the substitution is on the nitrogen atom rather than the a-carbon. This allows peptoids to be made using the so-called "sub-monomer" route. The side chain is derived from a simple primary amine, hundreds of which can be purchased inexpensively. It is important to note that peptoids are not restricted to the 20 known natural amino acids. Hence, any amine can be attached to the nitrogen, In contrast to pure peptoids, "hybrids" are molecules consisting of both N-substituted monomers (peptoids) and peptide monomers (D- or L-peptides). While peptoid monomers are proteolytically stable and available by the hundreds, there are some advantages to including peptide monomers. Both D- and L-peptide monomers can be incorporated into the backbone, although L-peptides are proteolytically unstable. D-peptides are proteolytically stable, as natural proteases are stereospecific and unable to cleave the peptide bond in the D analog. An overlap of D-peptides and peptoids would reveal overlapping backbone structure, but R groups, which are planar in the peptoid, are not planar in the D-peptide. Thus, the incorporation of D-peptides introduces chirality to the otherwise planar peptoid side groups. Furthermore, D-peptides introduce stability to the otherwise 'floppy' peptoid. D-peptides are energetically favored in the trans conformation, making them less floppy and more stable (adding similar advantages as the cyclic peptoids by increasing backbone rigidity). These hybrid D-peptide/peptoid compounds can be synthesized by incorporating well-developed peptide synthesis protocols into the submonorner peptoid synthesis protocols. The D-peptide monomers are merely more shapes added to the library.

B. Peptide Synthesis

The cyclic peptides of the present invention may be readily synthesized by known conventional procedures for the formation of a peptide linkage between amino acids. Such conventional procedures include, for example, any solution phase procedure permitting a condensation between the free alpha amino group of an amino acid residue having its carboxyl group and other reactive groups protected and the free primary carboxyl group of another amino acid residue having its amino group or other reactive groups protected. In a preferred conventional procedure, the cyclic peptides of the present invention may be synthesized by solid-phase synthesis and purified according to methods known in the art. Any of a number of well-known procedures utilizing a variety of resins and reagents may be used to prepare the cyclic peptides of the present invention.

The process for synthesizing the cyclic peptides may be carried out by a procedure whereby each amino acid residue in the desired sequence is added one at a time in succession to another amino acid residue or by a procedure whereby peptide fragments with the desired amino acid sequence are first synthesized conventionally and then condensed to provide the desired peptide. The resulting peptide is then cyclized to yield a cyclic peptide of the invention.

Solid phase peptide synthesis methods are well known and practiced in the art. In such methods the synthesis of peptides of the invention can be carried out by sequentially incorporating the desired amino acid residues one at a time into the growing peptide chain according to the general principles of solid phase methods. These methods are disclosed in numerous references, including Merrifield (1985) and Barmy et al. (1980).

In chemical syntheses of peptides, reactive side chain groups of the various amino acid residues are protected with suitable protecting groups, which prevent a chemical reaction from occurring at that site until the protecting group is removed. Also common is the protection of the alpha amino group of an amino acid residue or fragment while that entity reacts at the carboxyl group, followed by the selective removal of the alpha amino protecting group to allow a subsequent reaction to take place at that site. Specific protecting groups have been disclosed and are known in solid phase synthesis methods and solution phase synthesis methods. Alpha amino groups may be protected by a suitable protecting group, including a urethane-type protecting group, such as benzyloxycarbonyl (Z) and substituted benzyloxycarbonyl, such as p-chlorobenzyloxycarbonyl, p-nitrobenzyloxycarbonyl, p-bromobenzyloxycarbonyl, p-biphenyl-isopropoxycarbonyl, 9-fluorenylmethoxycarbonyl (Fmoc) and p-methoxybenzyloxycarbonyl (Moz) and aliphatic urethane-type protecting groups, such as t-butyloxycarbonyl (Boc), diisopropylmethoxycarbonyl, isopropoxycarbohyl, and anyloxycarbonyl (Alloc). Fmoc is preferred for alpha amino protection. Guanidino groups may be protected by a suitable protecting group, such as nitro, p-toluenesulfonyl (Tos), Z, pentamethylchromanesulfonyl (Pmc), adamantyloxycarbonyl, pentamethylhydrobenzofuran-5-sulfonyl (Pbf) and Boc. Pbf and Pmc are preferred protecting groups for Arg.

Solid phase synthesis is commenced from the C-terminal end of the peptide by coupling a protected alpha amino acid to a suitable resin. Such starting material is prepared by attaching an alpha amino-protected amino acid by an ester linkage to a p-benzytoxybenzyl alcohol (Wang) resin, a 2-chlorotrityl chloride resin or an oxime resin, by an amide bond between an Fmoc-Linker, such as p-[(R, S)-α-[1-(9H-fluor-en-9-yl)-methoxyformamido]-2,4-dimethyloxybenzyl]-phenoxyacctic acid (Rink linker) to a benzhydrylamine (BHA) resin, or by other means well known in the art. Fmoc-Linker-BHA resin supports are commercially available and generally used when feasible. The resins are carried through repetitive cycles as necessary to add amino acids sequentially. The alpha amino Fmoc protecting groups are removed under basic conditions. Piperidine, piperazine, diethylamine, or morpholine (20-40% v/v) in N,N-dimethylformamide (DMF) may be used for this purpose.

Following removal of the alpha amino protecting group, the subsequent protected amino acids are coupled stepwise in the desired order to obtain an intermediate, protected peptide-resin. The activating reagents used for coupling of the amino acids in the solid phase synthesis of the peptides are well known in the art. After the peptide is synthesized, if desired, the orthogonally protected side chain protecting groups may be removed using methods well known in the art for further derivatization of the peptide. Typically, orthogonal protecting groups are used as appropriate. For example, the peptides of the invention contain multiple amino acids with an amino group-containing side chain. In one aspect, an Allyl-Alloc protection scheme is employed with the amino acids forming a lactam bridge through their side chains, and orthogonal protecting groups, cleavable under different reactive conditions, used for other amino acids with amino group-containing side chains. Thus, for example, Fmoc-Lys(Pbf)-OH and Fmoc-Glu(OAII)-OH amino acids (Glu(OAH) refers to glutamic acid 5-allyt ester) can be employed for the positions forming a lactam bridge upon cyclization, while other amino acids with amino group-containing side chains have a different and orthogonal protecting group, such as with Fmoc-Arg (Pbf)-OH, Fmoc-Orn(Alloc)-OH, Fmoc-Dab(Pbf)-OH or the like. Other protecting groups may be similarly employed; by way of example and not limitation, Mtt/OPp (4-methyltrityl/2-phenylisopropyl) can be employed with the side chains forming a lactam bridge upon cyclization, with orthogonal protecting groups being utilized for other positions that are not cleavable using conditions suitable for cleavage of Mtt/OPp.

Reactive groups in a peptide can be selectively modified, either during solid phase synthesis or after removal from the resin. For example, peptides can be modified to obtain N-terminal modifications, such as acetylation, while on resin, or may be removed from the resin by use of a cleaving reagent and then modified. Similarly, methods for modifying side chains of amino acids are well known to those skilled in the art of peptide synthesis. The choice of modifications made to reactive groups present on the peptide will be determined, in part, by the characteristics that are desired in the peptide.

1. Cyclization

The peptides of the present disclosure are cyclized. Any method of cyclization may be employed.

a. Amide Formation

The peptide can, in one embodiment, be cyclized prior to cleavage from the peptide resin. For cyclization through reactive side chain moieties, the desired side chains are deprotected, and the peptide suspended in a suitable solvent and a cyclic coupling agent added. Suitable solvents include, fir example DMF, dichloromethane (DCM) or 1-methyl-2-pyrrolidone (NMP). Suitable cyclic coupling reagents include, for example, 2-(1H-benzotriazol-1-yl)-1,1,3,3-tetramethyluronium tetrafluoroborate (TBTU), 2-(1H-benzotriazol-1-yl)-1,1,3,3-tetramethyluronium hexafluorophosphate (HBTU), benzotriazole-1-yl-oxy-tris(dimethylamino)phosphonium-hexafluorophosphate (BOP), benzotriazole-1-yl-oxy-tris (pyrrolidino)phosphoniumhexafluorophosphate (PyBOP), 2-(7-aza-1H-benzotriazol-1-yl)-1, 1,3,3-tetramethyturonium tetratluoroborate (TATU), 2-(2-oxo-1(2H)-pyridyl)-1,1,3,3-tetramethyluronium tetrafluoroborate (TPTU) or N,N'-dicyclohexylcarbodiimide/i-hydroxybenzotriazole (DCCl/HOBt). Coupling is conventionally initiated by use of a suitable base, such as N,N-diisopropylethylatnine (DIPEA), sym-collidine or N-methylmorpholine (NMM).

The cyclized peptides can then be cleaved from solid phase, using any suitable reagent, such as ethylamine in DCM or various combinations of agents, such as trifluoroacetic acid (TFA), tri-isopropylsilane (TIS), dimethoxybenezene (DMB), water and the like. The resulting crude peptide is dried and remaining amino acid side chain protecting groups, if any, are cleaved using any suitable reagent, such as TFA in the presence of water, TIS, 2-mercaptopethane (ME), and/or 1,2-ethanedithiol (EDT). The final product may be precipitated by adding cold ether and collected by filtration. Final purification is by reverse phase high performance liquid chromatography (RP-HPLC), using a suitable column, such as a C18 column, or other methods of separation or purification, such as methods based on the size or charge of the peptide, may also be employed. Once purified, the peptide can be characterized by any number of methods, such as high performance liquid chromatography (HPLC), amino acid analysis, mass spectrometry, and the like.

For peptides of the present invention which have a C-terminus substituted amide derivative or N-alkyl group, synthesis may proceed by solid phase synthesis commenced from the C-terminal end of the peptide by coupling a protected alpha amino acid to a suitable resin. Such methods for preparing substituted amide derivatives on solid-phase have been described in the art. See, for example, Barn et al. (1996); DeGrado and Kaiser (1982). Such a starting material can be prepared by attaching an alpha amino-protected amino acid by an ester linkage to a p-benzyloxybenzyl alcohol (Wang) resin, by amide linkage to a 4-(2',4'-dimethoxyphenyl-aminomethyl-phenoxy (Rink Amide) resin, or an oxime resin, by well known means. The peptide chain is grown with the desired sequence of amino acids. Before cleavage, the peptide is cyclized on the solid phase, and the peptide-resin treated with a solution of appropriate amine (such as methyl amine, dimethyl amine, ethylamine, and so on). Peptides employing a p-benzyloxybenzyl alcohol (Wang) resin may be cleaved from resin by aluminum chloride in DCM, peptides employing a Rink Amide resin may be cleaved by mixture of TEA, TIS and water, and peptides employing an oxime resin may be cleaved by DCM. While synthesis has been described primarily with reference to solid phase Fmoc chemistry, it is to be understood that other chemistries and synthetic methods may be employed to make the cyclic peptides of the invention, such as by way of example and not limitation, methods employing Boc chemistry, solution chemistry, and other chemistries and synthetic methods.

b. Stapled Peptides

Hydrocarbon alpha helix stapled peptides have been developed and reported to be more stable and able to enter the cell (Zhang et al., 2011). The general approach for "stapling" a peptide is that two key residues within the peptide are modified by attachment of linkers through the amino acid side chains. Once synthesized, the linkers are connected through a catalyst, thereby creating a bridge the physically constrains the peptide into its native a-helical shape. In addition to helping retain the native structure needed to interact with a target molecule, this conformation also provides stability against peptidases as well as cell-permeating properties. U.S. Pat. Nos. 7,192,713 and 7,183,059, describing this technology, are hereby incorporated by reference. See also Schafmeister et al., 2000.

The stapled peptides may be synthesized according to the protocols described by Young-Woo Kim et al, (Young-Woo et al., 2011). Briefly, the construction of the peptide is carried out using Fmoc based solid phase synthesis. During the synthesis, the two alpha methyl, a-alkenyl amino acids are incorporated at positions separated by the desired number of intervening amino acids residues. The assembled peptides are then subjected in ruthenium-catalyzed ring closing metathesis (RCM) to form the macrocyclic hydrocarbon cross-link.

2. Lipidation

For lipidation, a lipid chain can be a C12 to C20 lipid chain. C16 and C18 lipid chains are preferred. The cyclic peptides can be lipidated by any conventional or acceptable method known in the art to introduce lipids to peptides. This can be achieved by attaching one or more lipid amities to the peptides. There are several ways for introducing lipids. The lipids can be attached via an oligopeptide spacer at either the N- or C-terminus of the peptides between the peptide and the lipid moiety. The oligopeptide can comprise any number of amino acid residues and the lipid moiety can be attached to any of the amino acid residues in the oligopeptide. The lipid moiety may be bulky and may be added to the N-terminal end of the oligopeptide such that it is separated from the amino acids of the peptide to prevent any possible interference with functional portions, for example, of the amino acids in the cyclic peptides. A suitable spacer may be selected for the particular application used. Usually, a spacer comprises no more than 3 amino acids that are relatively simple in structure (such as, but not limited to, serine, glycine or asparagine, for example). Serine is suitable as it increases the solubility of lipidated peptides in water. Also, it is advantageous to include lysine in the oligopeptide, which permits the addition of two lipid moieties. Alternatively, the peptides can be lipidated directly without using a spacer at all. In this way, either the N- or C-terminal amino acid residue of the peptide is itself lipidated. Finally, the peptide can undergo total lipidation, i.e., one or more residues of the peptide can be lipidated. One advantage of total lipidation is that the peptides can be purified first, then lipidated. This overcomes some of the problems associated with the purification of lipidated peptides.

Peptides need not be lipidated, but it may be advantageous for certain peptides to be lipidated with any acceptable lipid, such as palmitic acid (C16) or stearic acid (C18), so as to allow a peptide to pass through a lipid bilayer. Peptides incorporating lipidation may benefit from placement of a KSS motif at their N-termini. The peptides incorporating lipidation may contain one or more lipid moieties, for example, two lipid moieties per peptide. Lipidated peptides may move more easily through the cytoplasm and lipid bilayer, 3. PEGylation PEGylation is a method well known to those skilled in the art wherein a polypeptide or peptidomimetic compound (for the purposes of the present invention, a cyclic peptide LSD1 inhibitor or the functional analogue or variant) is modified such that one or more polyethylene glycol (PEG) molecules are covalently attached to the side chain of one or more amino acids or derivatives thereof. Other molecule altering structural chemistry techniques may be used; such techniques may improve the pharmacodynamic properties of the molecule, for example extending its half-life in vivo. A PEG-protein conjugate is formed by first activating the PEG moiety so that it will react with, and couple to, the protein or peptidomimetic compound of the invention. PEG moieties vary considerably in molecular weight and conformation, with the early moieties (monofunctional mPEGs; mPEGs) being linear with molecular weights of 12 kDa or less, and later moieties being of increased molecular weights, PEG2, a recent innovation in PEG technology, involves the coupling of a 30 kDa (or less) mPEG to a lysine amino acid (although. PEGylation can be extended to the addition of PEG to other amino acids) that is further reacted to form a branched structure that behaves like a linear mPEG of much greater molecular weight (Kozlowski et al., 2001). Methods that may be used to covalently attach the PEG molecules to polypeptides are further described in Roberts et al. (2002), Bhadra et al. (2002), Kozlowski et al. (2001), Veronese (2001), and references referred to therein.

The advantages of PEGylation of the peptide or peptidomimetic compounds of the invention include prolonged circulatory time due to reduced renal clearance resulting from increased hydrodynamic size (size in solution) of the agent which, for some products, results in a more sustained adsorption after administration as well as restricted distribution, possibly leading to a more constant and sustained plasma concentrations and hence an increase in clinical effectiveness (Harris et al., 2001). Further advantages can include reduced immunogenicity of the therapeutic compound (Reddy, 2001), and lower toxicity (Kozlowski etal., 2001).

The first step in PEGylation is the suitable functionalization of the PEG polymer at one or both terminals. PEGs that are activated at each terminus with the same reactive moiety are known as "homobifunctional", whereas if the functional groups present are different, then the PEG derivative is referred as "heterbifunctional" or "heterofunctional." The chemically active or activated derivatives of the PEG polymer are prepared to attach the PEG to the desired molecule.

The choice of the suitable functional group for the PEG derivative is based on the type of available reactive group on the molecule that will be coupled to the PEG. For proteins, typical reactive amino acids include lysine, cysteine, histidine, arginine, aspartic acid, glutamic acid, serine, threonine, tyrosine. The N-terminal amino group and the C-terminal carboxylic acid can also be used.

The techniques used to form first generation PEG derivatives are generally reacting the PEG polymer with a group that is reactive with hydroxyl groups, typically anhydrides, acid chlorides, chloroformates and carbonates. In the second generation PEGylation chemistry more efficient functional groups such as aldehyde, esters, amides etc. made available for conjugation.

As applications of PEGylation have become more and more advanced and sophisticated, there has been an increase in need for heterobifunctional PEGs for conjugation. These heterobifunctional PEGs are very useful in linking two entities, where a hydrophilic, flexible and biocompatible spacer is needed. Preferred end groups for heterobifunctional PEGs are maleimide, vinyl sulfones, pyridyl disulfide, amine, carboxylic acids and NHS esters.

The most common modification agents, or linkers, are based on methoxy PEG (MPEG) molecules. Their activity depends on adding a protein-modifying group to the alcohol end. In some instances polyethylene glycol (PEG diol) is used as the precursor molecule. The diol is subsequently modified at both ends in order to make a hetero- or homo-dimeric PEG-linked molecule (as shown in the example with PEG bis-vinylsulfone).

Proteins are generally PEGylated at nucleophilic sites such as unprotonated thiols (cysteinyl residues) or amino groups. Examples of cysteinyl-specific modification reagents include PEG maleimide, PEG iodoacetate, PEG thiols, and PEG vinylsulfone. All four are strongly cysteinyl-specific under mild conditions and neutral to slightly alkaline pH but each has some drawbacks. The amide formed with the maleimides can be somewhat unstable under alkaline conditions so there may be some limitation to formulation options with this linker. The amide linkage formed with iodo PEGs is more stable, but free iodine can modify tyrosine residues under some conditions. PEG thiols form disulfide bonds with protein thiols, but this linkage can also be unstable under alkaline conditions. PEG-vinylsulfone reactivity is relatively slow compared to maleimide and iodo PEG; however, the thioether linkage funned is quite stable. Its slower reaction rate also can make the PEG-vinylsultbne reaction easier to control.

Site-specific PEGylation at native cysteinyl residues is seldom carried out, since these residues are usually in the form of disulfide bonds or are required for biological activity. On the other hand, site-directed mutagenesis can be used to incorporate cysteinyt PEGylation sites for thiol-specific linkers. The cysteine mutation must be designed such that it is accessible to the PECiylation reagent and is still biologically active after PEGylation.

Amine-specific modification agents include PEG NHS ester, PEG tresylate, PEG aldehyde, PEG isothiocyanate, and several others. All react under mild conditions and are very specific for amino groups. The PEG NHS ester is probably one of the more reactive agents; however, its high reactivity can make the PEGylation reaction difficult to control at large scale. PEG aldehyde forms an imine with the amino group, which is then reduced to a secondary amine with sodium cyanoborohydride. Unlike sodium borohydride, sodium cyanoborohydride will not reduce disulfide bonds. However; this chemical is highly toxic and must be handled cautiously, particularly at lower pH where it becomes volatile.

Due to the multiple lysine residues on most proteins, site-specific PEGylation can be a challenge. Fortunately, because these reagents react with unprotonated amino groups, it is possible to direct the PEGylation to lower-pK amino groups by performing the reaction at a lower pH. Generally the pK of the alpha-amino group is 1-2 pH units lower than the epsilon-amino group of lysine residues. By PEGylating the molecule at pH 7 or below, high selectivity for the N-terminus frequently can be attained. However; this is only feasible if the N-terminal portion of the protein is not required for biological activity. Still, the pharmacokinetic benefits from PEGylation frequently outweigh a significant loss of in vitro bioactivity, resulting in a product with much greater in vivo bioactivity regardless of PEGylation chemistry.

There are several parameters to consider when developing a PEGylation procedure. Fortunately, there are usually no more than four or five key parameters. The "design of experiments" approach to optimization of PEGylation conditions can be very useful. For thiol-specific PEGylation reactions, parameters to consider include: protein concentration, PEG-to-protein ratio (on a molar basis), temperature, pH, reaction time, and in some instances, the exclusion of oxygen. (Oxygen can contribute to intermolecular disulfide formation by the protein, which will reduce the yield of the PEGylated product.) The same factors should be considered (with the exception of oxygen) for amine-specific modification except that pH may be even more critical, particularly when targeting the N-terminal amino group.

For both amine- and thiol-specific modifications, the reaction conditions may affect the stability of the protein. This may limit the temperature, protein concentration, and pH. In addition, the reactivity of the PEG linker should be known before starting the PEGylation reaction. For example, if the PEGylation agent is only 70 percent active, the amount of PEG used should ensure that only active PEG molecules are counted in the protein-to-PEG reaction stoichiometry.

III. Treatment of Disease

Certain aspects of the present embodiments can be used to prevent or treat a disease or disorder associated with overexpression of LSD1 or aberrant demethylation of H3K4 by LSD1. Functioning of LSD1 may be reduced by any suitable drugs to prevent the aberrant demethylation of H3K4 by LSD1. Preferably, such substances would be cyclic peptide inhibitor of LSD1.

"Treatment" and "treating" refer to administration or application of a therapeutic agent to a subject or performance of a procedure or modality on a subject for the purpose of obtaining a therapeutic benefit of a disease or health-related condition. For example, a treatment may include administration of a pharmaceutically effective amount of a cyclic peptide that inhibits LSD1.

"Subject" and "patient" refer to either a human or non-human, such as primates, mammals, and vertebrates. In particular embodiments, the subject is a human.

The term "therapeutic benefit" or "therapeutically effective" as used throughout this application refers to anything that promotes or enhances the well-being of the subject with respect to the medical treatment of this condition. This includes, but is not limited to, a reduction in the frequency or severity of the signs or symptoms of a disease. For example, treatment of cancer may involve, for example, a reduction in the size of a tumor, a reduction in the invasiveness of a tumor, reduction in the growth rate of the cancer, or prevention of metastasis. Treatment of cancer may also refer to prolonging survival of a subject with cancer.

A cyclic peptide that inhibits LSD1 may be administered to treat a cancer. The cancer may be a solid tumor, metastatic cancer, or non-metastatic cancer. In certain embodiments, the cancer may originate in the bladder, blood, bone, bone marrow, brain, breast, colon, esophagus, duodenum, small intestine, large intestine, colon, rectum, anus, gum, head, kidney, liver, lung, nasopharynx, neck, ovary, pancreas, prostate, skin, stomach, testis, tongue, or uterus.

The cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma ire adenomatous polyp; adenocarcinoma, familial polyposis con.; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonericapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma wlsquamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; malignant melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hernangiosarcorna; hemangioendotheliorna, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma.; retinoblastoma; olfactory neurogenic tumor; meningioma, malignant; neurofibrosarcoma; neurilemmoma, malignant; granular cell tumor, malignant; malignant lymphoma; hodgkin's disease; hodgkin's; paragranuloma; malignant lymphoma, small lymphocytic; malignant lymphoma, large cell, diffuse; malignant lymphoma, follicular; mycosis fungoides; other specified non-hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; mega.karyoblastic leukemia; myeloid sarcoma; and hairy cell leukemia.

A. Pharmaceutical Compositions

Where clinical application of a therapeutic composition containing an inhibitory cyclic peptide is undertaken, it will generally be beneficial to prepare a pharmaceutical or therapeutic composition appropriate for the intended application. This will typically entail preparing a pharmaceutical composition that is essentially free of pyrogens, as well as any other impurities that could be harmful to humans or animals. One may also employ appropriate buffers to render the complex stable and allow for uptake by target cells. In certain embodiments, pharmaceutical compositions may comprise, for example, at least about 0.1% of an active compound. In other embodiments, an active compound may comprise between about 2% to about 75% of the weight of the unit, or between about 25% to about 60%, for example, and any range derivable therein.

The phrases "pharmaceutical or pharmacologically acceptable" refers to molecular entities and compositions that do not produce an adverse, allergic, or other untoward reaction when administered to an animal, such as a human, as appropriate. The preparation of a pharmaceutical composition comprising a cyclic peptide or additional active ingredient will be known to those of skill in the art in light of the present disclosure. Moreover, for animal (e.g., human) administration, it will be understood that preparations should meet sterility, pyrogenicity, general safety, and purity standards as required by FDA Office of Biological Standards.

As used herein, "pharmaceutically acceptable carrier" includes any and all aqueous solvents (e.g., water, alcoholic/aqueous solutions, saline solutions, parenteral vehicles, such as sodium chloride, Ringer's dextrose, etc.), non-aqueous solvents (e.g., propylene glycol, polyethylene glycol, vegetable oil, and injectable organic esters, such as ethyloleate), dispersion media, coatings, surfactants, antioxidants, preservatives (e.g., antibacterial or antifungal agents, anti-oxidants, chelating agents, and inert gases), isotonic agents, absorption delaying agents, salts, drugs, drug stabilizers, gels, binders, excipients, disintegration agents, lubricants, sweetening agents, flavoring agents, dyes, fluid and nutrient repienishers, such like materials and combinations thereof, as would be known to one of ordinary skill in the art. The pH and exact concentration of the various components in a pharmaceutical composition are adjusted according to well-known parameters.

The term "unit dose" or "dosage" refers to physically discrete units suitable for use in a subject, each unit containing a predetermined quantity of the therapeutic composition calculated to produce the desired responses discussed above in association with its administration, i.e., the appropriate route and treatment regimen. The quantity to be administered, both according to number of treatments and unit dose, depends on the effect desired.

The actual dosage amount of a composition of the present embodiments administered to a patient or subject can be determined by physical and physiological factors, such as body weight, age, health, and sex of the subject, the type of disease being treated, the extent of disease penetration, previous or concurrent therapeutic interventions, idiopathy of the patient, the route of administration, and the potency, stability, and toxicity of the particular therapeutic substance. For example, a dose may also comprise from about 1 µg/kg/body weight to about 1000 mg/kg/body weight (this such range includes intervening doses) or more per administration, and any range derivable therein. In non-limiting examples of a derivable range from the numbers listed herein, a range of about 5 µg/kg/body weight to about 100 mg/kg/body weight, about 5 µg/kg/body weight to about 500 mg/kg/body weight, etc., can be administered. The practitioner responsible for administration will, in any event, determine the concentration of active ingredient(s) in a composition and appropriate dose(s) for the individual subject.

The active compounds can be formulated for parenteral administration, formulated for injection via the intravenous, intramuscular, sub-cutaneous, or even intraperitoneal routes. Typically, such compositions can be prepared as either liquid solutions or suspensions; solid forms suitable tier use to prepare solutions or suspensions upon the addition of a liquid prior to injection can also be prepared; and, the preparations can also he emulsified.

The pharmaceutical forms suitable for injectable use include sterile aqueous solutions or dispersions; formulations including sesame oil, peanut oil, or aqueous propylene glycol; and sterile powders for the extemporaneous preparation of sterile injectable solutions or dispersions. In all cases the form must be sterile and must he fluid to the extent that it may be easily injected. It also should be stable under the conditions of manufacture and storage and must be preserved against the contaminating action of microorganisms, such as bacteria and fungi.

The proteinaceous compositions may be formulated into a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also he derived from inorganic bases such as, for example, sodium, potassium, ammonium, calcium, or ferric hydroxides, and such organic bases as isopropylamine, trimethylamine, histidine, procaine and the like.

A pharmaceutical composition can include a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion, and by the use of surfactants. The prevention of the action of microorganisms can be brought about by various antibacterial and antifungal agents, for example, parabens, chiorobutanol, phenol, sorbic acid, thimerosal, and the like. In many cases, it will be preferable to include isotonic agents, fir example, sugars or sodium chloride. Prolonged absorption of the injectable compositions can be brought about by the use in the compositions of agents delaying absorption, for example, aluminum monostearate and gelatin.

Solutions of therapeutic compositions can be prepared in water suitably mixed with a surfactant, such as hydroxypropylcellulose. Dispersions also can be prepared in glycerol, liquid polyethylene glycols, mixtures thereof and in oils. Under ordinary conditions of storage and use, these preparations contain a preservative to prevent the growth of microorganisms.

The therapeutic compositions of the present invention may be administered in the form of injectable compositions either as liquid solutions or suspensions; solid forms suitable for solution in, or suspension in, liquid prior to injection may also be prepared. These preparations also may be emulsified.

Additional formulations are suitable for oral administration, Oral formulations include such typical excipients as, for example, pharmaceutical grades of mannitol, lactose, starch, magnesium stearate, sodium saccharine, cellulose, magnesium carbonate and the like. The compositions take the form of solutions, suspensions, tablets, pills, capsules, sustained release formulations or powders.

The therapeutic compositions of the present invention may include classic pharmaceutical preparations. Administration of therapeutic compositions according to the present invention will be via any common route so long as the target tissue is available via that route. This includes oral, nasal, buccal, rectal, vaginal or topical. Topical administration may be particularly advantageous for the treatment of skin cancers. Alternatively, administration may be by orthotopic, intradermal, subcutaneous, intramuscular, intraperitoneal or intravenous injection. Such compositions would normally be administered as pharmaceutically acceptable compositions that include physiologically acceptable carriers, buffers or other excipients. For treatment of conditions of the lungs, or respiratory tract, aerosol delivery can be used. Volume of the aerosol is between about 0.01 mL and 0.5 mL.

An effective amount of the therapeutic composition is determined based on the intended goal. For example, one skilled in the art can readily determine an effective amount of a cyclic inhibitory peptide of the invention to be administered to a given subject. The term "unit dose" or "dosage" refers to physically discrete units suitable for use in a subject, each unit containing a predetermined-quantity of the therapeutic composition calculated to produce the desired responses discussed above in association with its administration, i.e., the appropriate route and treatment regimen. The quantity to be administered, both according to number of treatments and unit dose, depends on the protection or effect desired.

Precise amounts of the therapeutic composition also depend on the judgment of the practitioner and are particular to each individual. Factors affecting the dose include the physical and clinical state of the patient, the route of administration, the intended goal of treatment and the potency, stability and toxicity of the particular therapeutic substance.

B. Combination Treatments

In certain embodiments, the compositions and methods of the present embodiments involve a cyclic peptide LSD1 inhibitor to inhibit the aberrant demethylation of H3K4 by LSD1, in combination with a second or additional therapy. Such therapy can be applied in the treatment of any disease that is associated with aberrant demethylation of H3K4 by LSD1. For example, the disease may be cancer.

The methods and compositions, including combination therapies, enhance the therapeutic or protective effect, and/or increase the therapeutic effect of another anti-cancer or anti-hyperproliferative therapy. Therapeutic and prophylactic methods and compositions can be provided in a combined amount effective to achieve the desired effect, such as the killing of a cancer cell and/or the inhibition of cellular hyperproliferation. This process may involve contacting the cells with both a cyclic inhibitoty peptide and a second therapy. A tissue, tumor, or cell can be contacted with one or more compositions or pharmacological formulation(s) comprising one or more of the agents (i.e., cyclic peptide or an anti-cancer agent), or by contacting the tissue, tumor, and/or cell with two or more distinct compositions or formulations, wherein one composition provides 1) a cyclic peptide, 2) an anti-cancer agent, or 3) both a cyclic peptide and an anti-cancer agent. Also, it is contemplated that such a combination therapy can be used in conjunction with chemotherapy, radiotherapy, surgical therapy, or immunotherapy.

The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing, for example, both agents are delivered to a cell in a combined amount effective to kill the cell or prevent it from dividing.

An inhibitory cyclic peptide may be administered before, during, after, or in various combinations relative to an anti-cancer treatment. The administrations may be in intervals ranging from concurrently to minutes to days to weeks. in embodiments where the cyclic peptide is provided to a patient separately from an anti-cancer agent, one would generally ensure that a significant period of time did not expire between the time of each delivery, such that the two compounds would still be able to exert an advantageously combined effect on the patient. In such instances, it is contemplated that one may provide a patient with the cyclic peptide and the anti-cancer therapy within about 12 to 24 or 72 h of each other and, more particularly, within about 6-12 h of each other. In some situations it may be desirable to extend the time period for treatment significantly where several days (2, 3, 4, 5, 6, or 7) to several weeks (1, 2, 3, 4, 5, 6, 7, or 8) lapse between respective administrations.

In certain embodiments, a course of treatment will last 1-90 days or more (this such range includes intervening days). t is contemplated that one agent may be given on any day of day 1 to day 90 (this such range includes intervening days) or any combination thereof and another agent is given on any day of day 1 to day 90 (this such range includes intervening days) or any combination thereof. Within a single day (24-hour period), the patient may be given one or multiple administrations of the agent(s). Moreover, after a course of treatment, it is contemplated that there is a period of time at which no anti-cancer treatment is administered. This time period may last 1-7 days, and/or 1-5 weeks, and/or 1-12 months or more (this such range includes intervening days), depending on the condition of the patient, such as their prognosis, strength, health, etc. It is expected that the treatment cycles would be repeated as necessary.

Various combinations may be employed. For the example below a cyclic peptide therapy is "A" and an anti-cancer therapy is "B":

A/B/A B/A/B B/B/A A/A/B A/B/B B/A/A A/B/B/B B/A/B/B
B/B/B/A B/B/A/B A/A/B/B A/B/A/B A/B/B/A B/B/A/A
B/A/B/A B/A/A/B A/A/A/B B/A/A/A A/B/A/A A/A/B/A

Administration of any compound or therapy of the present embodiments to a patient will follow general protocols for the administration of such compounds, taking into account the toxicity, if any, of the agents. Therefore, in some embodiments there is a step of monitoring toxicity that is attributable to combination therapy.

1. Chemotherapy

A wide variety of chemotherapeutic agents may be used in accordance with the present embodiments. The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis.

Examples of chemotherapeutic agents include alkylating agents, such as thiotepa and cyoslhosphamide; alkyl sulfonates, such as busulfan, itnprosulfan, and piposulfan; aziridines, such as benzodopa, carboquone, meturedopa, and uredopa; ethylenimines and methylamelamines, including altretamine, triethylenemelamine, trietylenephosphoramide, triethiylenethiophosphoramide, and trimethylolomelamine; acetogenins (especially bullatacin and bullatacinone); a camptothecin (including the synthetic analogue topotecan); bryostatin; callystatin; CC-1065 (including its adozelesin, carzeiesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards, such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, and uracil mustard; nitrosureas, such as carmustine, chlorozotocin, fotemustine, lomustine, nimustine, and ranimnustine; antibiotics, such as the enediyne antibiotics (e.g., calicheamicin, especially calicheamicin gammaII and calicheamicin omega11); dynemicin, including dynemicin A; bisphosphonates, such as clodronate; an esperamicin; as well as neocarzinostatin chromophore and related chromoprotein enediyne antiobiotic chromophores, aclacinomysins, actinomycin, authrarnycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxortibicin, cyanomorphotino-doxorubicin, 2-pyrrolino-doxorubicin and deoxydoxorubicin), epirubicin, esorubicin, idarubicin, marcellomycin, mitomycins, such as mitomycin C, mycophenolic acid, nogalarnycin, olivomycins, peplornycin, potfiromycin, puromycin, quelamycin, rodorubicin, streptonigrin, streptozocin, tubercidin, ubenirnex, zinostatin, and zorubicin; anti-metabolites, such as methotrexate and 5-fluorouracil (5-FU); folic acid analogues, such as denopterin, pteropterin, and trimetrexate; purine analogs, such as fludarabine, 6-mercaptopurine, thiamiprine, and thioguanine; pyrimidine analogs, such as ancitabine, azacitidine, 6-azauridine, carmofur, cytarabine, dideoxyuridine, doxifluridine, enocitabine, and floxuridine; androgens, such as calusterone, dromostanolone propionate, epitiostanol, mepitiostane, and testolactone; anti-adrenals, such as mitotane and trilostane; folic acid replenisher, such as frolinic acid; aceglatone; aldophosphamide glycoside; aminolevulinic acid; eniluracil; amsacrine; bestrabucil; bisantrene; edatraxate; defofatnine; demecolcine; diaziquone; elformithine; elliptinium acetate; an epothilone; etoglucid; gallium nitrate; hydroxyurea; lentinan; lonidainine; maytansinoids, such as maytansine and ansamitocins; mitoguazone; mitoxantrone; mopidanmol; nitraerine; pentostatin; phenamet; pirarubicin; losoxantrone; podophyilinic acid; 2-ethylhydrazide; procarbazine; PSKpolysaccharide complex; razoxane; rhizoxi n; sizofi ran ; spi rogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; taxoids, e.g., paclitaxel and docetaxel gemcitabine; 6-thioguanine; mercaptopurine; platinum coordination complexes, such as cisplatin, oxatiplatin, and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan CPT-11); topoisomerase inhibitor RFS 2000; difiuorometlhylomithine (DMFO); retinoids, such as retinoic acid; capecitabine; carboplatin, procarbazine,plicomycin, gemcitabien, navelbine, farnesyl-protein tansferase inhibitors, transplatinum, and pharmaceutically acceptable salts, acids, or derivatives of any of the above.

2. Radiotherapy

Other factors that cause DNA damage and have been used extensively include what are commonly known as γ-rays, X-rays, and/or the directed delivery of radioisotopes to tumor cells. Other forms of DNA damaging factors are also contemplated, such as microwaves, proton beam irradiation (U.S. Pat. Nos. 5,760,395 and 4,870,287), and UV-irradiation. It is most likely that all of these factors affect a broad range of damage on DNA, on the precursors of l)NA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic 3. Immunotherapy The skilled artisan will understand that additional immunotherapies may be used in combination or in conjunction with methods of the embodiments. in the context of cancer treatment, immunotherapeutics, generally, rely on the use of immune effector cells and molecules to target and destroy cancer cells. Rituximab (RITUXAN®) is such an example. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

In one aspect of immunotherapy, the tumor cell must bear some marker that is amenable to targeting, i.e., is not present on the majority of other cells. Many tumor markers exist and any of these may be suitable for targeting in the context of the present embodiments. Common tumor markers include CD20, carcinoembryonic antigen, tyrosinase (p97), gp68, TAG-72, FIMFG, SialylLe-svis Antigen, MucA, MucB, PLAP, laminin receptor, erb B, and p155. A alternative aspect of immunotherapy is to combine anticancer effects with immune stimulatory effects. Immune stimulating molecules also exist including: cytokines, such as 1L-2, 1L-4, IL-12, GM-CSF, gamma-IFN, chemokines, such as MIP-1, MCP-1, IL-8 and growth factors, such as FLT3 ligand.

Examples of immunotherapies currently under investigation or in use are immune adjuvants, e.g., *Mycobacterium bovis, Plasmodium falciparum*, dinitrochlorobenzene, and aromatic compounds (U.S. Pat. Nos. 5,801,005 and 5,739,169; Elui and Hashimoto, 1998; Christodoulides et al., 1998); cytokine therapy, e.g., interferons α, β, and γ, IL-1, GM-CSF, and TNF (Bukowski et al., 1998; Davidson et al., 1998; Hellstrand et al., 1998); gene therapy, e.g., TNF, IL-1, IL-2, and p53 (Qin et al., 1998; Austin-Ward and Villaseca, 1998; U.S. Pat. Nos. 5,830,880 and 5,846,945); and monoclonal antibodies, e.g., anti-CD20, anti-ganglioside GM2, and anti-p185 (Hollander, 2012; Hanibuchi et al., 1998; U.S. Pat. No. 5,824,311). It is contemplated that one or more anti-cancer therapies may be employed with the antibody therapies described herein.

4. Surgery

Approximately 60% of persons with cancer will undergo surgery of some type, which includes preventative, diagnostic or staging, curative, and palliative surgery. Curative surgery includes resection in which all or part of cancerous tissue is physically removed, excised, and/or destroyed and may be used in conjunction with other therapies, such as the treatment of the present embodiments, chemotherapy, radiotherapy, hormonal therapy, gene therapy, immunotherapy, andior alternative therapies. Tumor resection refers to physical removal of at least part of a tumor. In addition to tumor resection, treatment by surgery includes laser surgery, cryosurgery, electrosurgery, and microscopically-controlled surgery (Mohs' surgery).

Upon excision of part or all of cancerous cells, tissue, or tumor, a cavity may be formed in the body. Treatment may be accomplished by perfusion, direct injection, or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

5. Other Agents

It is contemplated that other agents may be used in combination with certain aspects of the present embodiments to improve the therapeutic efficacy of treatment. These additional agents include agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Increases in intercellular signaling by elevating the number of GAP junctions would increase the anti-hyperproliferative effects on the neighboring hyperproliferative cell population. In other embodiments, cytostatic or differentiation agents can be used in combination with certain aspects of the present embodiments to improve the anti-hyperprotiferative efficacy of the treatments. Inhibitors of cell adhesion are contemplated to improve the efficacy of the present embodiments, Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with certain aspects of the present embodiments to improve the treatment efficacy.

IV. Kits

The present invention provides kits, such as therapeutic kits. For example, a kit may comprise one or more pharmaceutical composition as described herein and optionally instructions fur their use. Kits may also comprise one or more devices for accomplishing administration of such compositions. For example, a subject kit may comprise a pharmaceutical composition and catheter for accomplishing direct intravenous injection of the composition into a cancerous tumor. In other embodiments, a subject kit may comprise pre-filled ampoules of a cyclic peptide inhibitor of LSD1, optionally formulated as a pharmaceutical, or lyophilized, for use with a delivery device.

Kits may comprise a container with a label. Suitable containers include, for example, bottles, vials, and test tubes. The containers may be formed from a variety of materials such as glass or plastic. The container may hold a composition which includes a cyclic peptide that is effective for therapeutic or non-therapeutic applications, such as described above. The label on the container may indicate that the composition is used for a specific therapy or non-therapeutic application, and may also indicate directions for either in vivo or in vitro use, such as those described above. The kit of the invention will typically comprise the container described above and one or more other containers comprising materials desirable from a commercial and user standpoint, including buffers, diluents, filters, needles, syringes, and package inserts with instructions for use.

V. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Cyclic Peptide Inhibitors of LSD1

Peptides having less than 16 amino acid residues bind poorly to LSD1, and optimal binding appears to require 21 amino acid residues (Culhane et al., 2010). Thus, the inventors used ligand-based techniques to design and synthesize a series of linear and cyclic peptides based on the 21-amino acid histone 3 lysine 4 binding region. Because it is a potent peptide-based inhibitor of LSD1, the X-ray crystallographic structure of LSD1-CoREST bound to 8 was used as the basis for the design of these cyclic peptide inhibitors. The X-ray crystallographic conformation of the bound [Met]$^4$ H3 (1-21)-OH peptide revealed that the side chains of certain amino acid residues are in proximity to each other in three dimensions. For example Arg2 and Gln5, Arg2 and Ser10, Arg2 and Gly12, Arg2 and Lys14, and Gln5 and Ser10 were identified as pairs of amino acid residues situated in close proximity (FIG. 2) during LSD1 binding to 8.

To produce peptides that were constrained in the bound conformation of 8, the inventors designed and synthesized peptides substituted in select positions with one Lys residue and one Glu residue, and cyclized these residues to form a lactam bridge (Table 2). Compound 10-15 were substituted in selected positions with a Lys and a Glu residue, which were then cyclized by forming a lactam bridge. By choosing varied positions for the Lys and Glu used to form the lactam, peptides with different sized cyclic epitopes could be formed. Standard N-Fmoc/tert-Bu chemistry was used to construct all linear and cyclic peptide analogues in this study (see Table 2 for the structures of designed peptides and Example 2 for the chemical synthesis). Polystyrene resin with low substitution (0.36 mmol/g) was used as a polymer support to yield all peptides as C-terminal carboxyamides.

TABLE 2

Percent inhibition of LSD1 by cyclic peptide analogues at 10 μM.

| | Structure | % Inhib. of LSD1 at 10 μM |
|---|---|---|
| 8 | [Met]$^4$ H3 (1-21)-OH (H-AR$^2$TMQ$^5$TARK$^9$S$^{10}$TGGK$^{14}$APRKQLA-OH) (SEQ ID NO: 1) | 97 ± 2.5 |
| 9 | [Met]$^4$ H3 (1-21)-NH$_2$ (H-AR$^2$TMQ$^5$TARK$^9$S$^{10}$TGGK$^{14}$APRKQLA-NH$_2$) (SEQ ID NO: 1) | 91 ± 0.1 |
| 10 | C[Lys$^2$, Glu$^{14}$][Met]$^4$ H3 (1-21)-NH$_2$<br>┌─────────────────────────┐<br>----K$^2$------------------------------E$^{14}$--- | 39 ± 3.8 |

TABLE 2-continued

Percent inhibition of LSD1 by cyclic peptide analogues at 10 μM.

| | Structure | % Inhib. of LSD1 at 10 μM |
|---|---|---|
| 11 | C[Lys$^5$, Glu$^{10}$][Met]$^4$ H3 (1-21)-NH$_2$<br>⌐K$^5$────E$^{10}$┐ | 94 ± 0.3 |
| 12 | C[Lys$^2$, Glu$^{10}$][Met]$^4$ H3 (1-21)-NH$_2$<br>⌐K$^2$────E$^{10}$┐ | 48 ± 19 |
| 13 | C[Lys$^2$, Glu$^{12}$][Met]$^4$ H3 (1-21)-NH$_2$<br>⌐K$^2$────E$^{12}$┐ | 49 ± 0.6 |
| 14 | C[Lys$^2$, Glu$^5$][Met]$^4$ H3 (1-21)-NH$_2$<br>⌐K$^2$────E$^5$┐ | 43 ± 12 |
| 15 | C[Lys$^9$, Glu$^{14}$][Met]$^4$ H3 (1-21)-NH$_2$<br>⌐K$^9$────E$^{14}$┐ | 78 ± 0.4 |
| 3 | [structure of verlindamycin] | 95 ± 0.1 |

Where appropriate, N-Fmoc amino acids not used for the lactam bridge formation were side-chain protected with acid labile protecting groups (e.g., $^t$Bu, Boc, Trt and Pbt), whereas Lys and Glu residues used for lactam bridge formation were side-chain protected. using the orthogonal protecting groups alloc and allyl, respectively. The alloc and ailyl protecting groups were selectively removed using Pd(PPh$_3$)$_3$ in the presence of the allyl. scavenger DMBA. After removing the orthogonal protecting groups, and while the peptide chain was still attached to the resin, the lactam-bridge between the side chains of Lys and Glu was formed using the coupling reagent, Py BOP and a base, DIPEA. The protected cyclic or linear peptide was cleaved from the solid support using TEA and an appropriate scavenger. All target peptides were purified by column chromatography on a COMBIFLASH® purification system equipped with a C18 column. They were then fully characterized by UPLC, LC-MS, and high resolution MALDI spectrometry (Table 3).

Figure 3:
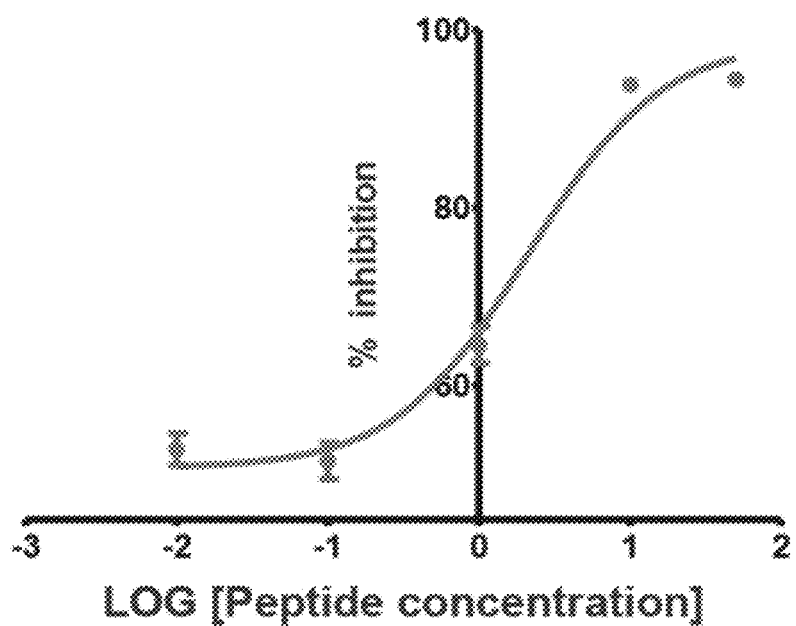
FIG. 3—Determination of the $IC_{50}$ value for 9 against purified recombinant LSD1. Inhibition values were gathered at concentrations between 0,01 and 50 μM.
Figure 8:
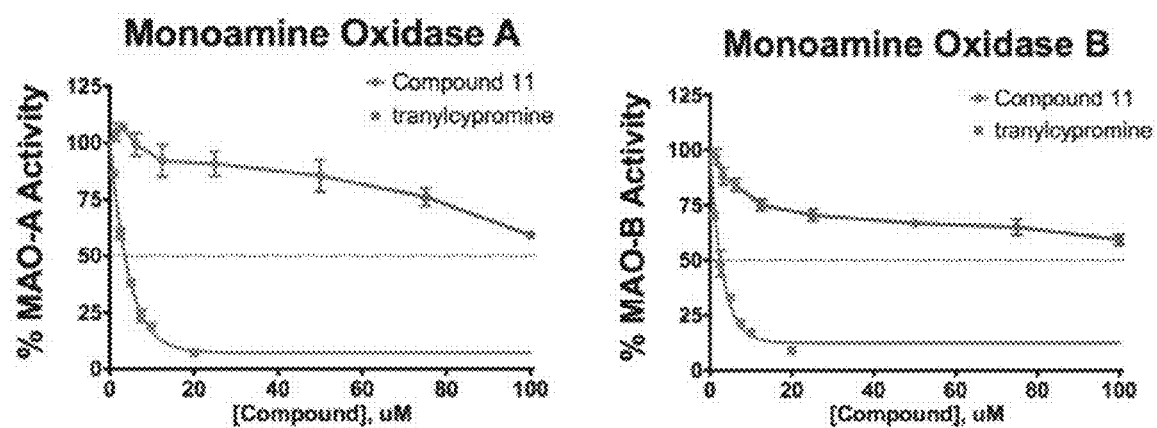
FIG. 8—$IC_{50}$ determination for cyclic peptide inhibitor 11 against human monoamine oxidase A and B in vitro. Each data point is the average of three determinations±standard error.
Figure 9:
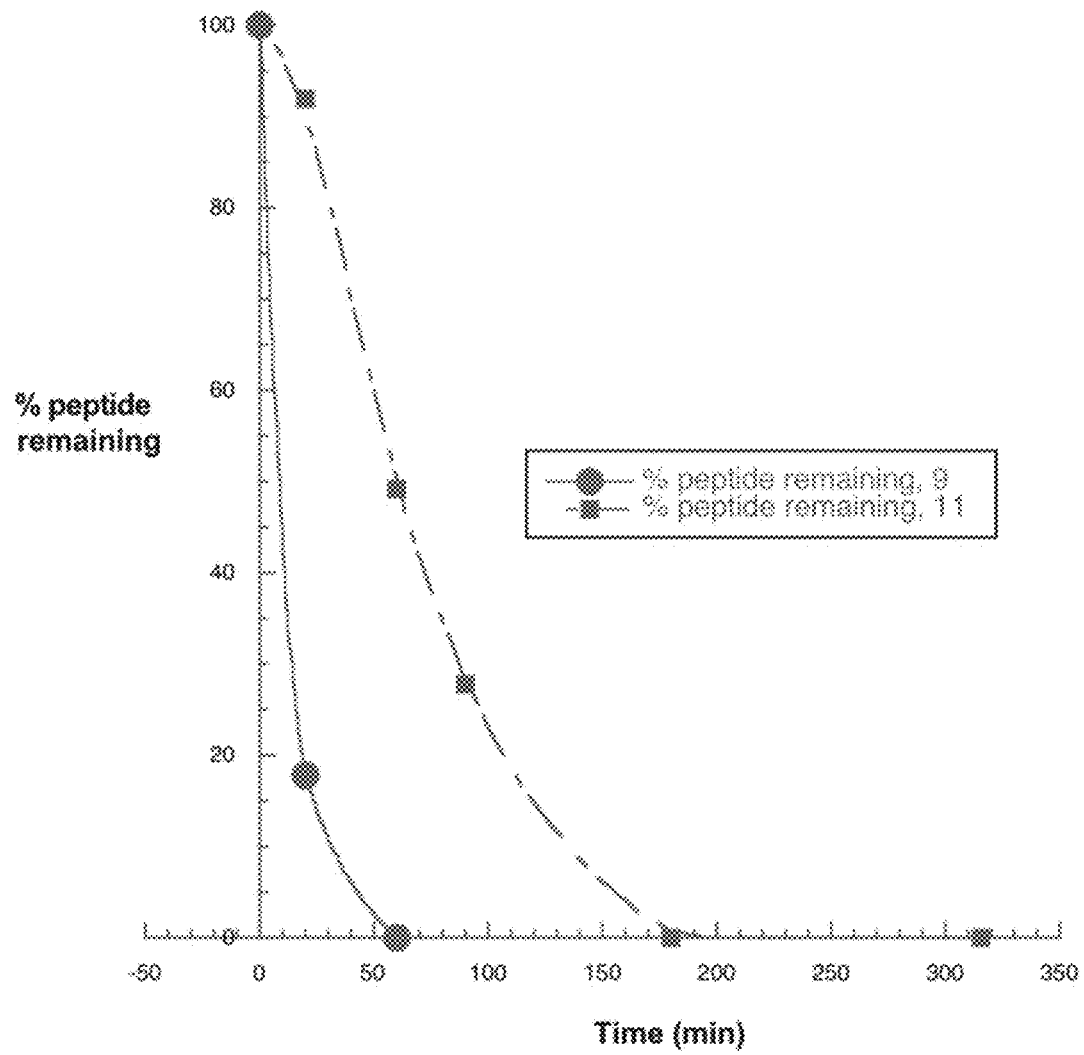
FIG. 9—Metabolic stability of linear peptide 9 and cyclic peptide 11 in rat plasma.

The level of LSD1 inhibition for all cyclic and linear peptides was evaluated using a previously described peroxide coupled assay (Fortneris et al., 2006; Zhou et al., 1997) in the presence of a fixed concentration of a peptide substrate containing a dimethylated lysine residue. Each compound was initially evaluated at a 10 μM. concentration (see Table 2), and an IC$_{50}$ value was determined for the most active peptide analogue, 11, over a concentration range of 0.01-50 μM. The known LSD1 inhibitor verlindamycin (3) (Huang et al., 2007) was used as a positive control, and produced 95% inhibition of the enzyme at 10 μM. This level of inhibition is consistent with previously published values (Sharma et al., 2010; Hazeldine et al., 2012). As shown in Table 2, all cyclic peptides inhibited the enzyme between 39% and 94% (Tables 2 and 5), following the relative rank order of 11>9>15>13=12>14>10. Thus the [Met]$^4$ H3 (1-21)-NH$_2$ cyclic peptide 11, in which the lactam bridge was between Lys5 and Glu 0, produced the greatest LSD1 inhibitory activity, while cyclic [Lys2, Glu14] [Met]$^4$ H3 (1-21)-NH$_2$ 10 displayed the least inhibitory activity. As shown in FIG. 3, the IC$_{50}$ value for inhibitor 11 against recombinant LSD1 was determined to be 2.1 μM, and it was found to be a competitive inhibitor with a K of 385 nM. Peptide 11 was highly selective for LSD1, and possessed an IC$_{50}$ value >100 μM for inhibition against MAO-A and MAO-B (FIG. 8). To assess the in vitro metabolic stability of linear peptide 9 and cyclic peptide 11, their half-lives for their hydrolytic degradation were determined in rat plasma at 25° C. (Yamamoto et al., 2009). As shown in FIG. 9, cyclic peptide 9 was >4-fold more stable (T$_{1/2}$=59.8 min) compared to the linear peptide 7 (T$_{1/2}$=14.3 min).

Both [Met]$^4$ H3 (1-21)-OH 8 and the corresponding carboxyamide [Met]$^4$ H3 (1-21)-NH$_2$ 9, which are identical in amino acid sequence but differ in their C-terminal functional group, were effective inhibitors, although 9 was somewhat less potent.

Figure 4:
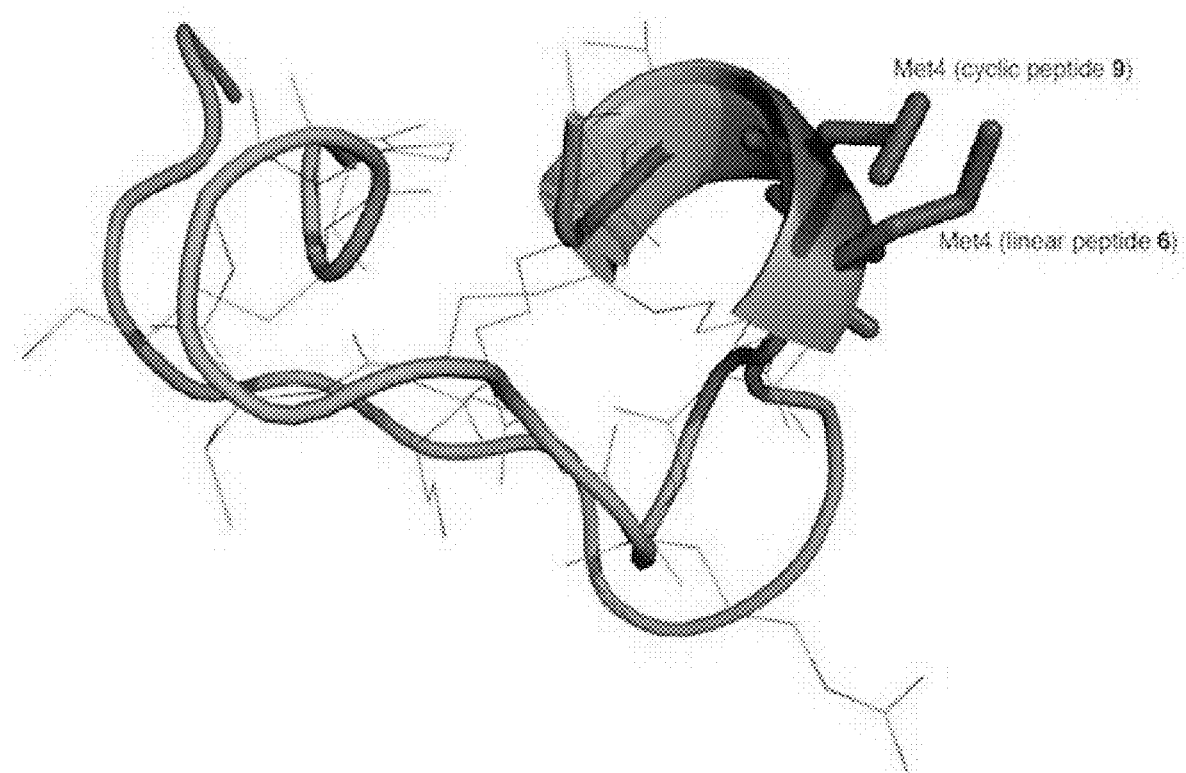
FIG. 4—Structural superimposition of linear peptide 6 and cyclic peptide 9. Amino acids 1-16 are shown for both peptides. The green color represents the X-ray crystallographic conformation of 6 as reported in the PDB file 2VID. The cyan color represents the global least energy conformation of cyclic peptide 9 derived from the MCMM algorithm of MacroModel. Met4 of 6 and 9 are shown in red and blue, respectively.

In order to understand the inhibitory activity of 11, it was compared to the reported X-ray crystallographic conformation of 8 in silico. The global least energy conformation of 11 was obtained using the Monte Carlo MACROMODEL® (MCMM) search algorithm (Chang et al., 1989; Saunders et al., 1990). As shown in FIG. 4, the least energy conformation of 11 features a right-handed alpha helical section and a beta sheet section. When the MCMM-derived conformation of amino acid residues 1-16 of 11 was compared with that of 8, the compounds were found to assume very similar backbone and local side chain conformations. The similarity in least energy conformations of the cyclic peptide H and the linear [Met]⁴ H3 (1-21)-OH 8 could explain their similar ability to inhibit recombinant LSD1.

Figure 5:
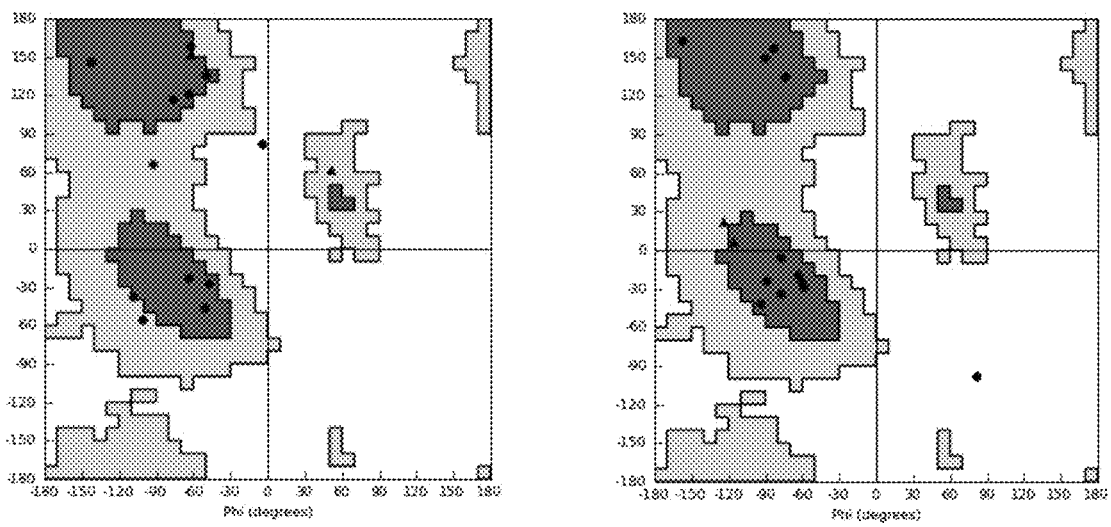
FIG. 5—Ramachandran plots generated from Maestro. Left panel: The Ramachandran plot of X-ray crystallographic conformation of [Met]$^4$ H3 (1-21)-OH [PDB code: 2VID]. Right panel: The Ramachandran plot of global minimum energy conformation of 9. Only the amino acids (1-16) of both peptides were shown in the Rarnachandran plots.
Figure 6:
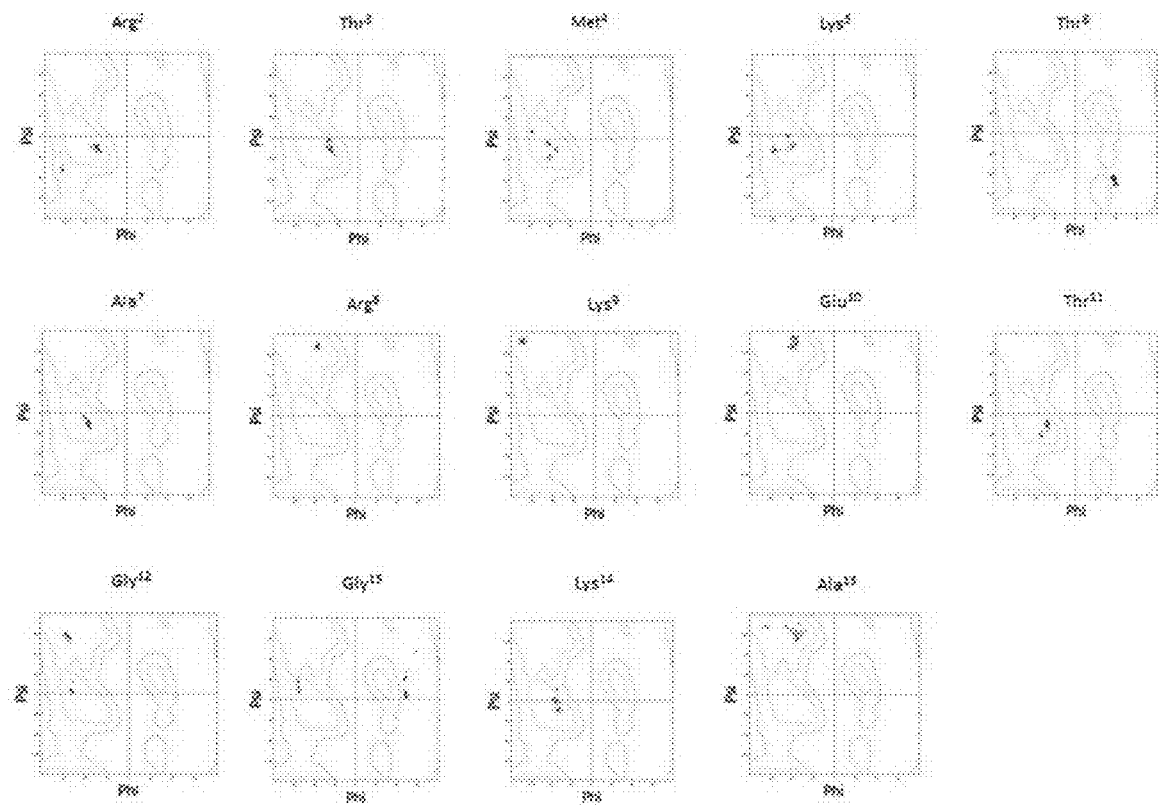
FIG. 6—Φ and ψ dihedral angle distributions (i.e., Ramachandran plots) of the resultant 50 energetically lowest structures obtained from the MCMM algorithm calculations for each amino acid in the peptide 9—amino acids (1-16).
Figure 7:
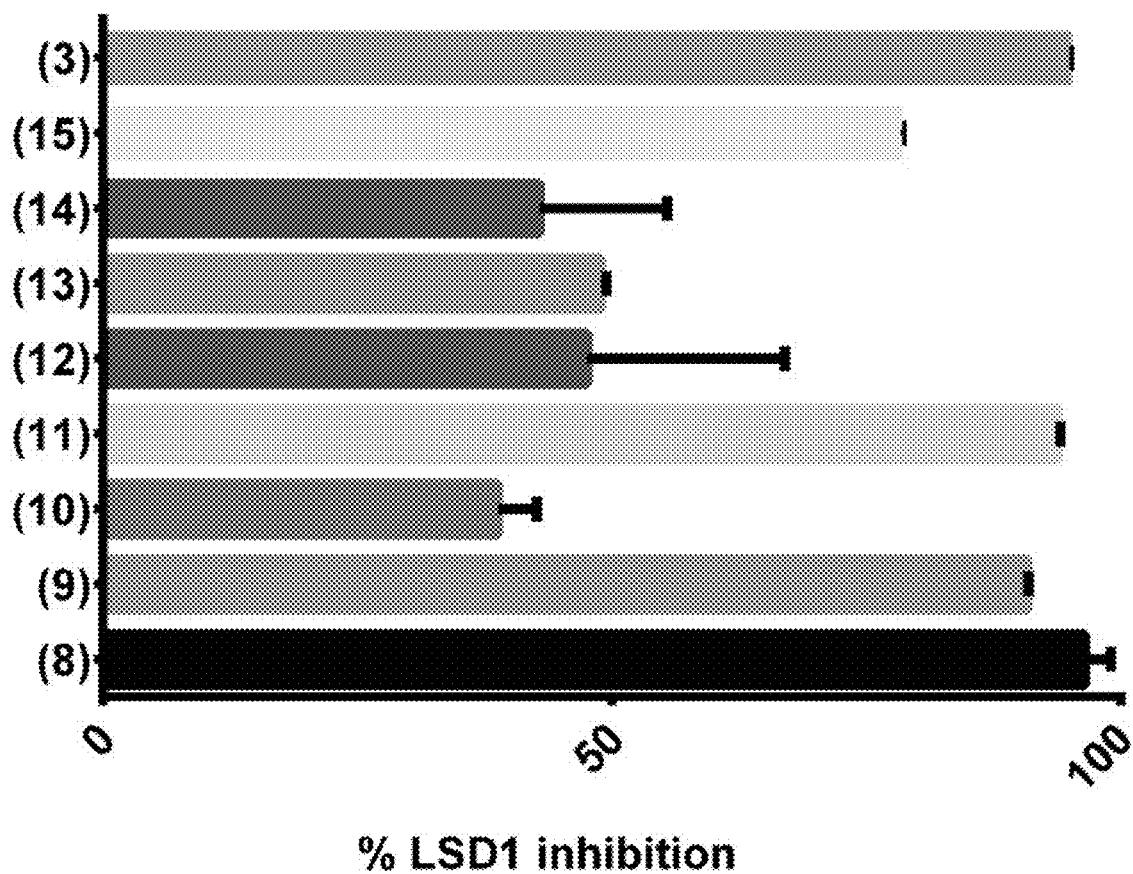
FIG. 7—Percentage of LSD1 inhibition assay of cyclic and linear peptides. Each data point is the average of three determinations.

Comparison of the 50 lowest energy conformations of 11 obtained from MCMM analysis was assessed by the distribution of their backbone dihedral angles φ and ψ in a Ramachandran plot as shown in FIGS. 5 and 6. Almost all the amino acids except Gly12 and Gly13 display very narrow range of distribution of dihedral angles. This confirms that there can be a rigid conformation in all the amino acids except Gly12 and Gly13. Two groups of amino acid residues, one containing Arg8, Lys9, Glu10 and Ala15 and the other containing Arg2, Thr3, Met4, Lys5, Lys14 fall in the distinct regions of beta sheet and right-handed alpha helix in Rarnachandran plot, respectively.

Interestingly, the dihedral angle for the Gly12 promotes a right-handed. alpha helix or a beta sheet, whereas Gly12 promotes a right-handed alpha helix or a left-handed alpha helix (see, FIG. 6). Moreover, Thr6 falls into an energetically unfavorable region of the Ramachandran plot (FIG. 5). It appears that Thr6 adopts a strained conformation due to the local constraint introduced by cyclization.

Inhibitors 3, 9 and 11 were evaluated for their growth inhibitory effect in the MCF-7 breast and Calu-6 lung tumor lines in vitro using an MTS cell viability assay (Cory et al., 1991; Izumiyama et al., 2003). At 72 hours, inhibitors 9 and 11 displayed $IC_{50}$ values of 152.6 and 156.6 µM in MCF-7 cells and 120.7 and 125.3 µM in Calu-6 cells, compared to $IC_{50}$ values of 5,9 and 10.9 µM for 3 in MCF-7 and Calu-6 cells, respectively. The relatively low growth inhibitory potency following treatment with 9 and 11 as compared to 3 could be due to reduced transport into the cell and/or nucleus. However, membrane penetration can be enhanced through modification of the cyclic peptide structure, as described below.

Example 2

Optimization of Cyclic Peptide-Based Inhibitors of LSD1

An alanine scanning approach will be used to determine which amino acid residues in the cyclic portion of the lead peptide are critical for binding to the LSD1 active site. Then, peptidomimetic and peptoid residues will be systematically substituted into the cyclic structure of our lead peptide to enhance enzyme inhibitory activity, improve cell penetration and increase stability in plasma. Analogues of the lead peptide that feature lysine residues at position 4 that are substituted with warhead groups will be produced. Cyclic peptide inhibitors selected by predetermined criteria will be lipidated to determine enhanced delivery and/or oral activity and ultimately create the potential for selective targeting of tumor cells.

Ligand-based techniques will be used as previously described (Kumarasinghe and Woster, 2014) to design a series of cyclic peptides based on the 21-amino acid H3K4 substrate, using the X-ray structure of LSD1-CoREST bound to 8 as the basis for inhibitor design. The ability of each peptide to inhibit recombinant LSD1 will be determined, and activity against monoamine oxidase A and B will be monitored as a measure of target selectivity. Selected active inhibitors (LSD1 $IC_{50}$<1 µM and/or $K_i$<100 nM) will be considered for cell culture evaluation. Prior to cell culture studies, each peptide selected using the criteria above will be evaluated for metabolic stability in rat plasma as described above. Inhibitors with a plasma T1/2 of 60 minutes or more will be evaluated against two tumor cell lines in culture, both alone, and in combination with the DNA methyltransferase inhibitor 5-azacytidine (5-AC). Subsequent changes in H3K4 methylation and tumor suppressor protein expression will be monitored by Western blotting. Inhibitors meeting predetermined criteria (significant increases in H3K4me, re-expression of tumor suppressor genes) will be lipidated to enhance delivery into tumor cells, and then re-evaluated. Finally, the in vivo efficacy of selected compounds will be determined using a murine xenograft approach.

In order to optimize the structure of the cyclic peptide lead 11, standard methods will be used for introducing stability, enhancing cell permeability and maximizing fit to the active site. The selection of substitutions will be guided by a structure-based design approach, in which putative inhibitor molecules will be modeled into the active site of LSD1 prior to their synthesis, as previously described (Fomeris et al., 2007; Kumarasinghe and Woster, 2014), The synthetic approaches below are meant to serve as examples, and a library of cyclic peptide analogues can be synthesized for each approach. Selection of new analogues will be guided by the biological activity of previous entries in the library.

Alanine scanning. Before designing additional inhibitor peptides, an alanine scan will be performed on the lead molecule 11, focusing on the amino acid residues in and near the cyclic epitope (1-9). Although the residues important for binding of the linear inhibitor 8 are known, there may be some differences in the binding mode for 11, and thus it will be determined which residues can be altered without destroying inhibitory activity. Briefly, each residue will be replaced by an alanine, first virtually and then by peptide synthesis, and the activity of each mutant will be determined. When amino acids are identified where structural changes are tolerated, systematic substitution of peptide residues will be undertaken as described below.

Scheme 1

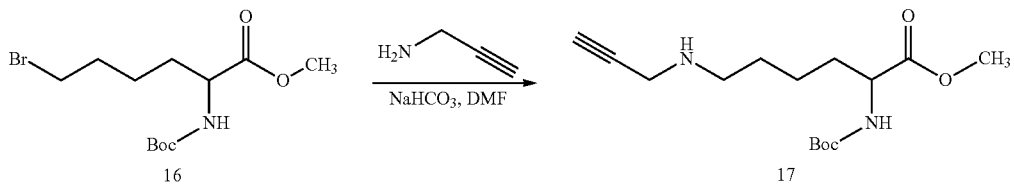

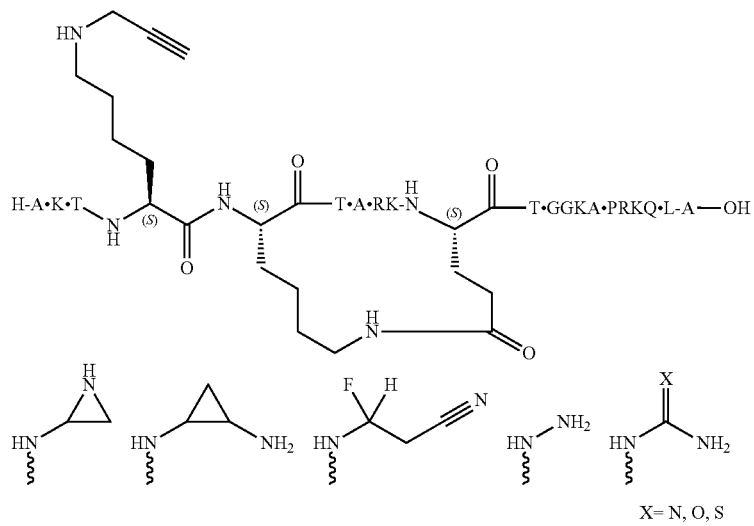

18

X= N, O, S

Modified lysine residues. A library of analogues of 8 in which Met4 is replaced by a modified lysine can be produced as shown in Scheme 1. Substitutions on the ε-amino group of lysine can range from simple alkyl or aralkyl to an activatable functional group. For example, propargyllysine derivatives have been shown to act as effiNtive inhibitors of LSD 1 in vitm (Suzuki and Miyata, 2011; Culhane et al., 2006; Schmitt et al., 2013). The synthesis of N-propargyllysine 17 can be accomplished in a single step by reacting the protected bromoamino acid 16 with propargyl amine. Orthogonal deprotection of the methyl ester or the N-Boc protecting group will then allow incorporation of 17 into a cyclic peptide to yield 18. A similar scheme can be used to produce appropriately functionalized lysine residues to yield versions of 18 with N-aziridino-, N-2-aminocyclopropyl-, activatable N-3-fluoropropionitrile (activated by proton abstraction and elimination of the fluorine to form a Michael acceptor), hydrazino-, guanidino, ureado, thioureado, etc. Amino acid equivalents carefully designed to form bonding interactions with the LSD1 active site can also be inserted in place of residues 1-12, as dictated by structure-based analysis, to enhance binding to the LSD1 catalytic site. This approach will thus allow formation of both competitive inhibitors and irreversible inactivators of LSD1.

Peptide-to-peptoid substitutions. Incorporation of peptoid residues with carefully selected side chains can be used to create mimics of natural peptide surfaces, making them suitable for use in inhibitor design (Horne, 2011). Thus, peptoid residues will be incorporated into predetermined positions in the cyclic peptide structure, again guided by structure-based in silico design. Peptoid intermediates can be readily generated under microwave conditions as shown in Scheme 2, and used for incorporation into peptides by an automated synthesizer (Olivos et al, 2002). An appropriate amine 19, representing the side chain of the desired amino acid is reacted with 2-bromoacetate 20 in THF to produce the corresponding amino-ester 21. N-Fmoc protection of the secondary amine (Fmoc-OSu) (Gawande and Branco, 2011) followed by ester cleavage (LiOH) then yields the desired peptoid monomer 22. Using peptoid amino acid equivalents, peptides that have homogeneous (all peptoid) or heterogeneous (mix of amino acids/peptoid) (Olsen, 2010) backbones can be constructed (Home, 2011). Because the peptoid bond features a tertiary rather than a secondary amine, these linkages are slow to hydrolyze, and thus lend stability to the peptide. importantly, peptoid monomers can be inserted at any desired backbone position(s).

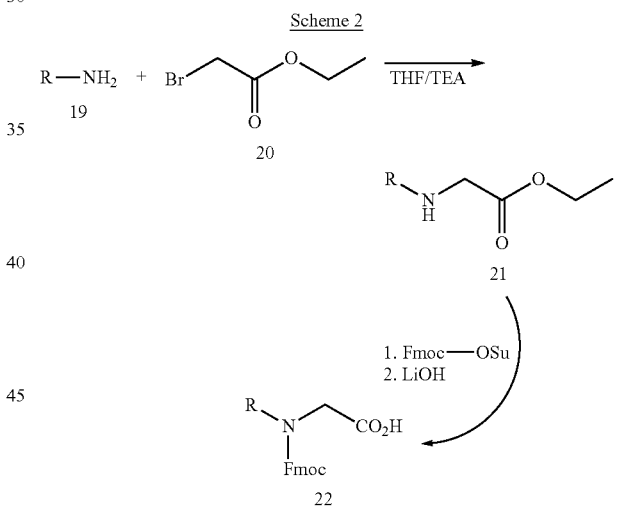

N-methylated amino acid residues. N-methyl substitution of an a-amino acid restricts the amide bond, eliminates hydrogen-bond donating ability, affects backbone torsional angles and allows the formation of a cis peptide bond. in addition, N-methyl-amino-acid scans can be used to evaluate the extent to which backbone conformational restriction affects biological activity (Hruby, 2002). N-methyl amino acids can be purchased or readily and stereospecifically produced from the corresponding N-nosyl amino acid by forming the corresponding 2-oxophenylacyl ester, N-methylation and deprotection (Leggio et al., 2010).

Figure 10:
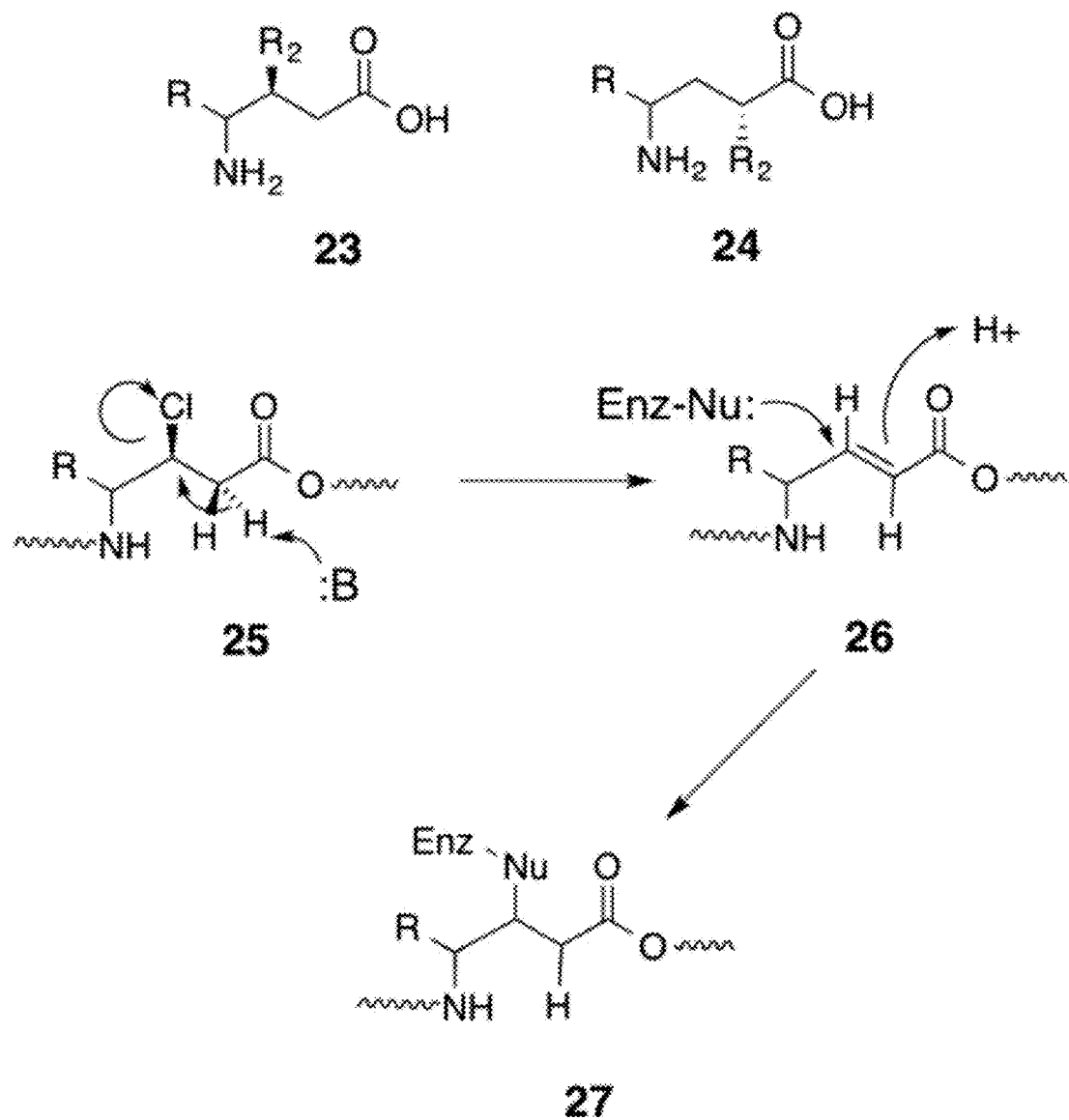
FIG. 10—Examples of β-amino acid substitutions.

Incorporation of substituted β-amino acids. The use of β-amino acids in the design of peptidomimetics is a well known method for conferring stability to hydrolysis (Seeback et al., 2004). Thus, substituted n-amino acids such as 23 and 24 (FIG. 10) will be used in the cyclic peptide inhibitors, with the goal of reducing proteolysis and increasing lipid solubility by adding hydrophobic substituents at R and $R_2$. In addition, the inclusion of a latent electrophile (such as in 25) would allow abstraction of a proton in the catalytic site, followed by β-elimination and formation of a Michael acceptor. Attack by a nucleophilic amino acid residue would then form a covalently-bound inhibitor and inactivate the enzyme, Cyclization methods. Strategically placed lysine and glutamate residues will be used in the analogue structure to facilitate formation of a cyclic epitope through amide formation. In addition, the "stapled peptide" method will be used to form cyclic cell-penetrating peptides (CPPs) with enhanced biological properties. Incorporation of an all-hydrocarbon "staple" into peptides can greatly increase their alpha-helix propensity, leading to an improvement in pharmaceutical properties such as proteolytic stability, target affinity, and cell permeability (Kim et al, 2011; Shim et al., 2013; Verdine and Hilinski, 2012; Schafmeister et al., 2000). The secondary structure of 11 contains two groups of amino acid residues, one containing Arg8, Lys9, Glu10 and Ala15 (a β-sheet) and the other containing Arg2, Thr3, Met4, Lys5, Lys14 (a right handed α-helix). Peptide stapling will be used to produce the cyclic epitope, as shown in Scheme 3. In the example, the 21-mer peptide 28 is constructed with olefinic side-chain monomers at positions 5 and 10, and the cyclic epitope is formed by ring-closing metathesis (RCM) to form 29 using Grubbs catalyst (Verdine and Hilinski, 2012). By altering the number of carbons in the olefinic side chains, or the position of the olefinic groups in the peptide chain, larger or smaller cyclic epitopes can be produced (Shim et al., 2013).

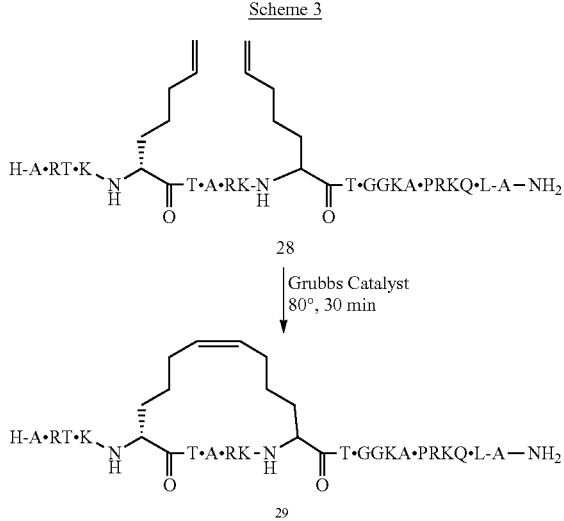

Scheme 3

Lipidation of cyclic peptide analogues. Lipidation confers additional resistance to proteolysis (Lee et at., 1999), and improves membrane permeability, bioavailability, and peptide pharmacokinetic and pharmacodynamic properties (Zhang and Bulaj, 2012). Initially, C16-C18 fatty acids or polyethylene glycol (PEG) will be appended to amino acid monomers prior to their incorporation into the peptide at selected positions. Because there are no sulfur-containing amino acids in the parent peptide, fatty acids will be added through amide or ester bonds with the appropriate amino acid side chains.

Characterization of cyclic peptide analogues. All amino acid residues and their surrogates, and all completed peptides, will be purified by silica gel chromatography, or by C18 column chromatography. Purified intermediates and final products will then be fully characterized by NMR spectroscopy and LC-MS analysis. Purity of intermediates and final cyclic peptide products will be determined by UPLC analysis, and final compounds will be certified as >95% pure prior to use in assay or in vivo procedures.

Example 3

Cyclic Peptide LSD1 Inhibitors Affect Tumor Growth in viva

The efficacy of cyclic peptides satisfying predetermined criteria will be evaluated in a murine xenograft model of tumor growth. Specifically, SCID mice bearing tumors from the Calu-6 human lung adenocarcinoma line and the MDA-MB-231 hormone receptor negative breast tumor line will be treated.

LSD1 inhibitors with the highest potency will be evaluated in vivo for their toxicity and biodistribution, and to determine their efficacy in murine xenograft models of human cancer. For these xenografts, the Calu-6 human lung adenocarcinoma line and the MDA-MB-231 human breast tumor will be used, and in vivo efficacy will be determined with the peptide alone and in combination with 5-AC.

Criteria ,Ibr selection of compounds for testing. In vivo testing will be conducted with the newly-synthesized LSD1 inhibitors. The key criteria for selection of compounds for in vivo testing will be their selectivity and potency for inhibition of LSD1 and their antitumor effect as measured in intact cells. Further considerations for compound selection will include: amenability to synthesis on a gram scale, the ease of lipidation, the predicted. pharmacokinetic behavior of the compounds and structural novelty.

Toxicity and pharmacodynamic assessments. It is necessary to establish the maximum-tolerated dose (MTD) for repeated administration of each LSD1 inhibitor before its ability to inhibit tumor growth can be assessed in the xenograft model. Groups of three Swiss-Webster female mice will receive intravenous injections of the LSD1 inhibitor preparation dissolved in PEG400 at an initial dose of 50 mg/kg. The animals will be monitored for at least 8 h for toxicity. The same dose of the test compound will be administered daily for 5 days per week tier 3 weeks for a total of 15 doses. Dose-escalation or reduction will follow a modified Fibonacci sequence until ⅔ of the animals demonstrate toxic effects. The next lower dose will be taken as the MTD.

Pharmacokinetic and biodistribution studies. Groups of three Swiss-Webster mice will be treated with the test LSD1 inhibitor preparation at its MTD. At times of 0, 1, 2, 4, 8 and 24 h, the animals will be sacrificed, and the blood, brain, liver and kidneys will be harvested. Samples of the plasma and tissues will be extracted and analyzed for the test compound by UPLC. If necessary, i.e. half-lives are greater than 8 h, later time points will be added in repeated experiments, Noncompartmental and compartmental analyses will be applied to the observed plasma drug concentration-time data (AUC) to yield estimates of the total systemic clearance ($CL_1$), volume of distribution at steady-state (VSS) and the elimination half-life. Rapid elimination will indicate the need for more frequent dosing, and the biodistribution may indicate sites of potential toxicity, Evaluation of the efA:cts of cyclic peptide LSD1 inhibitors on tumors in vivo. The key criteria for selection of compounds for efficacy testing will be: low toxicity, suitable PKs (preferably $T_{1/2}$>8 h) and broad biodistribution. Once tolerated doses have been established, Calu-6 or MDA-MB-231 tumor cells from log phase culture will be implanted into mice by injection of $10^7$ tumor cells subcutaneously. The Calu-6 and MDA-MB-231 lines form palpable tumors within 3-4 weeks, When the tumors reach 100-200 mm in volume as determined by caliper, the animals will be randomized into three groups for treatment. I.V. injections of the appropriate concentration of each inhibitor in a volume of 0.2 mL will start at this time. The selected LSD1 inhibitor alone will be compared to the combination of the LSa1 inhibitor plus 5-AC, and to saline control. When 5-AC is used it will be dosed at 1-2 mg/kg/day×5 I.V. as previously published Belinsky et al., 2003). Initial treatment protocols will consist of three cycles of 5 days on treatment with the selected LSD1 inhibitor followed by two days off. For combination studies with 5-AC, the 5-day course will be accompanied by a 5 day treatment of 5-AC. Alternative treatment schedules will be considered based on the results from the initial trials, Animals in each of the three cycle treatment groups will be followed for the determination of antitumor drug effects using time to progression-Kaplan-Meier analysis. Progression is defined as a tumor volume 4 times the volume of the tumor at initiation of treatment as we have previously reported (Hacker et al., 2008). The logrank test will be used to determine the statistical significance of any tumor response. Differences will be considered statistically significant if $p<0.05$. Tumors will be measured and volumes will be estimated weekly. Once progression is established, animals will be sacrificed and tissue will be harvested for analysis as described above. Positive results in these model systems will be valuable in the design and performance of clinical trials for promising compounds. As in the case in the in vitro cell-based assay procedures, the in vivo experiments described can also be adapted for use in the study of other tumor lines.

In the efficacy studies, differences among treatment groups will be tested. using the Random Effects/Autoregressive Errors mathematical model described by Heitjen et al. (1993), which provides more accurate estimation of the type 1 error (false-positive) rate than do more common simple statistical comparisons. Compounds will be considered to have antitumor activity if Tumor Growth Inhibition is greater than 60%. Quantitative endpoints such as body weight will be compared by repeated measure one-way ANOVA with statistical significance set at $p<0.05$. Drug doses will be adjusted if necessary during the course of the experiments due to excessive weight loss or signs of systemic toxicity.

Example 4

Experimental Section

Chemical synthesis. $N^\alpha$-Fmoc amino acids were purchased from Advanced Chemtech (Louisville, Ky.) and AAPPTcc (Louisville, Ky.). Fmoc-rink linker and aminomethylated polystyrene resin was purchased from the Novabiochem (Gibbstown, N.J.). Reagent grade Piperidine was purchased from Sigma Aldrich. All the other solvents were purchased from MR and Fisher and used without further purification. All of the cyclic and linear peptide analogues were synthesized by using standard Nα-Fmoc/tBu solid-phase peptide synthesis. A three channel PS3 automated peptide synthesizer from Protein Technologies, Inc. Tucson Ariz. was used for peptide synthesis, The aminomethylated polystyrene resin (0.25 mmol, 0.36 mmol/g) was placed in a 40 mL glass reaction vessel in the synthesizer and allowed to swell in 15 mL of DME solution for 30 min. Then the resin was washed with 15 mL of DMF (3×2min), The Fmoc linker was introduced to the swelled resin using mixture of Fmoc linker (1.0 mmol, 4 equiv), HBTU (1 mmol, 4 equiv), and NMM (2 mmol, 8 equiv) in DMF for 60 min. After coupling of the Emoc linker to the resin, the resin was washed with 15 mL of DMF solution (5×2 min.). The Fmoc protecting group on the resin was removed with 15 mL of 20% piperidine in DMF (2×15 min) followed by washing with 15 mL of DMF (5×2 min). Then, a preactivated Fmoc-amino acid prepared by mixing a Fmoc-amino acid (4 equiv), HBTU (4 equiv), and NMM (8 equiv) in DMF was introduced into the reaction vessel, and the reaction was continued for 1 h. The deprotection and coupling steps were repeated for each amino acid until desired sequence was obtained.

For linear peptides, once the desired sequence was obtained on resin, it was washed with 15 mL of DMF (5×2 min), DCM (5×2 min) and methanol (5×2 min) and dried in the vacuum overnight at 0° C. Then it was allowed to cleave from the resin for 2.5 h using cleavage mixture of 18 mL containing TFA, 0.5 mL, of dimethylsulfide, 0.5 mL of 1,2-ethanedithiol, and 1 mL of thioanisole. The TFA solution containing cleaved peptide was filtered, and the resin was further washed with trifluoroacetic acid (10 mL). The combined TFA solution was concentrated to a volume of approximately 3 mL with a gentle stream of nitrogen, and the peptide was precipitated with cold diethyl ether (30 mL). The precipitated peptide was vortexed for 1 min and centrifuged. The ether solution was decanted to remove the scavengers. Washing with cold diethyl ether was repeated for four to five times and the peptide was dried in a vacuum.

For cyclic peptides, once the fully protected peptide having desired sequence is Obtained on resin (0.25 mmol), orthogonal protective groups of the peptide (alloc protecting groups of Lys and ailyl group of Glu) were selectively removed using mixture of $Pd(PPh_3)_4$ (30 mg, 0.1 equiv), and DMBA (390 mg, 10 equiv) in 6 mL DMF:DCM (1:3) in the 40 mL reaction vessel under $N_2$ atmosphere for 30 min twice. Then the resin was washed with 15 mL of DMF (5×2 min) and washed with 15 ml. of 0.1 M LiCl in DMF solution (3 x 2 min). It was again washed with 15 ml of DMF (3×2 min), The resin was treated with PyBOP/HOBt/DIPEA (6, 6, and 12 equiv) in 6 mL of DGM: DMF: NMP (1:1:1) for 6 h twice for formation of the lactam bridge. Then resin was washed with DMF (3×2 min) and the cyclic peptide was cleaved from the resin as very similar to the procedure described above for the linear peptide.

Structural characterization of cyclic peptides. The purified peptides were characterized by HRMS and LC-MS (See Table 3 for the characterization data for synthesized peptides). High resolution mass spectrometric data was taken in the positive ion mode using Brucker AUTOFLEX® III MALDI-TOF instrument. LC-MS data was obtained in the positive ion mode using Waters LC-MS instrument [having Waters 2545 quaternary gradient module, Waters 2767 sample manager, Waters SFO fluidic organizer, Waters 3100 mass detector containing single quadrapole, and Waters PDA detector 2998] on Waters XTERR® C18 column (3.0×100 mm, 5 μM ). UPLC chromatograms were obtained using a Waters AQUITY UPLC® (H class, PDA detector, sample manager FTN and quaternary solvent manager) fitted with a Waters BEH C18 column (2.1×100 mm, 1.7 μM).

TABLE 3

Characterization table for the cyclized and linear peptides synthesized in this study.

| | | Retention Time (min) | | | Molar Mass | | |
|---|---|---|---|---|---|---|---|
| | | | | | | Observed (m/z)[a] | Observed (m/z)[b] |
| Entry | Purity | $(t_r)_A$ | $(t_r)_B$ | Molecular formula | Calcd. | MALDI-TOF | LC-MS |
| (8) | >95 | 3.33 | 0.71 | C93H169N35O28S | 2256.26 | $(M + H)^+$ = 2255.968 | $[M + 3H]^{+3}$ = 753.92 |
| (9) | >95 | 0.22 | 0.82 | C93H170N36O27S | 2255.28 | $(M + H)^+$ = 2256.265 | $[M + 4H]^{+4}$ = 565.3 |
| (10) | >95 | 4.88 | 0.48 | C92H163N33O28S | 2210.21 | $(M + K)^+$ = 2249.323 $(M + H)^+$ = 2210.191 | $[M + 3H]^{+3}$ = 738.34 |
| (11) | >95 | 5.04 | 0.68 | C96H174N36O26S | 2279.31 | $(M + H)^+$ = 2279.064 | $[M + 3Na]^{+3}$ = 784.9 |
| (12) | >95 | 4.99 | 0.43 | C95H170N34O27S | 2251.27 | $(M + 2Na + K)^+$ = 2336.369 $(M + H)^+$ = 2251.185 | $[M + 4Fe]^{+4}$ = 619.00 $[M + 3Na]^{+3}$ = 775.47 |
| (13) | >95 | 0.18 | 0.70 | C96H172N34O28S | 2281.28 | $(M + 5K + 2H)^+$ = 2478.792 $(M + H)^+$ = 2281.905 | $[M + 2H]^+$ = 1142.63 |
| (14) | >95 | 5.20 | 0.50 | C93H167N33O27S | 2210.24 | $(M + Na + H)^+$ = 2234.396 $(M + H)^+$ = 2210.549 | $[M + 3H]^{+3}$ = 738.18 |
| (15) | >95 | 5.01 | 0.47 | C92H163N35O28S | 2238.21 | $(M + H)^+$ = 2309.838 | $[M + 3H]^{+3}$ = 747.53 |

Retention time $(t_r)_A$ was determined using Waters UPLC ® system running gradient 10-90% acetonitrile in H$_2$O over 10 min at flow rate of 0.5 mL/min and retention time $(t_r)_B$ was determined using Waters LC-MS system running gradient 10-90% acetonitrile in H$_2$O over 20 min at flow rate of 1.0 mL/min. Experimental observed mass for peptides (6)-(13) obtained by
[a]Bruker AUTOFLEX ® III MALDI-TOF and
[b]Waters LC-MS system having a single quadrapole.

Determination of the con formation of peptide ligands. Molecular modeling experiments employed MACROMODEL® 9 equipped with MAESTRO™ 9 graphical interface installed on an AMD quad core computer system. Peptide structures were built into extended structures with standard bond lengths and angles, all the charges of the functional groups of peptides at physiological pH=7.2 were taken into account, and they were minimized using the OPLS-AA force field and the Polak-Ribier conjugate gradient (PRCG). Optimizations were converged to a gradient root mean square deviation (RMSD) less that 0.005 kJ/Å mol or continued until a limit of 50,000 iterations was reached. Aqueous solution conditions were simulated using the continuum dielectric water solvent model (GB/SA) in MACROMODEL®. Extended cutoff distances were defined at 8 Å for van der Waals, 20 Å for electrostatics, and 4 Å for H-bonds.

Conformational analysis of the peptides was performed using the MACROMODEL® MCMM procedure and energy minimization parameters. A total of 1000 search steps were performed and confirmations with energy differences of 21 kJ/mol or less from the global minimum were saved. Interatomic distances and dihedral angles were measured for each peptide analogue using the standard MAESTRO™ measurement tool (Table 4).

In vitro LSD1 enzyme inhibition assay. The % LSD1 enzyme inhibition for the cyclic and linear peptides was determined in vitro (Yang et al., 2007; Forneris et al., 2007) using the LSD1 fluorescent assay kit from the BPS Biosciences (cat #50106) according to the manufacturer's instructions. The LSD1 assay kit comes with the 96 microtiter well plate, purified LSD1 recombinant enzyme. AMPLEX® red reagent, horseradish peroxidase reagent (HRP) and 2× LSD1 assay buffer for 96 enzyme reactions. The total final LSD1 assay volume was 50 μL. The assay was carried out in 96-well microtiter plates in triplicate. The stock solutions of the cyclic and linear peptides were prepared by dissolving them in sterile water and verlindamycin 3 was prepared by dissolving it in DMSO. All the succeeding dilutions for the test inhibitors and 3 were carried out in the LSD1 assay buffer. LSD1 inhibition of all test compounds were carried out at 10 μM fixed concentrations in final 50 μL of total assay volumes. Enzymatic reaction was initiated by adding methylated peptide substrate (200 μM) to LSD1 assay mixture contained LSD1 (150 ng), test inhibitor (50 μM) and 50 μL of solution containing mixture of 50 μL of 10 mM MANTA® red and 100 μL of 10 U/mL. HRP in 4850 mL of 1× LSD1 buffer. Positive control contained all the above components except test inhibitor. The substrate control contained all the above components

TABLE 4

Comparison of the dihedral angles (φ, ψ) of global minimum conformation of the cyclic peptide 11 and [Met]⁴ H3 (1-16)-OH found in the PDB ID: 2V1D.

| | Ala | | Arg² | | Thr | | Mel | | Gln | | Thr | | Ala | | Arg | |
|---|---|---|---|---|---|---|---|---|---|---|---|---|---|---|---|---|
| ID vs. Res. | φ | ψ | φ | ψ | φ | ψ | φ | ψ | φ | ψ | φ | ψ | φ | ψ | φ | ψ |
| [Met]⁴ H3 (1-16)-OH | — | — | −51 | −46 | −48 | −28 | −64 | −22 | −76 | 117 | −101 | −55 | −62 | 159 | −5 | 82 |
| (11) | — | — | −60 | −28 | −60 | −25 | −94 | −42 | −90 | −23 | 81 | −97 | −78 | −33 | −84 | 157 |

| | | Lys | | Ser | | Thr | | Gly | | Gly | | Lys¹⁴ | | Ala | |
|---|---|---|---|---|---|---|---|---|---|---|---|---|---|---|---|
| | ID vs. Res. | φ | ψ | φ | ψ | φ | ψ | φ | ψ | φ | ψ | φ | ψ | φ | ψ |
| | [Met]⁴ H3 (1-16)-OH | −63 | 121 | −50 | 136 | −109 | −37 | −63 | 152 | 51 | 62 | −143 | 146 | −93 | 66 |
| | (11) | −158 | 163 | −90 | 150 | −64 | −19 | −116 | 6 | −124 | 22 | −78 | −5 | −74 | 135 | except methylated peptide substrate and test inhibitor. The blank contained all the above components except test inhibitor. Assay components were incubated at room temperature for 25 min before reading the fluorescence at wavelengths 530 nm (excitation) and wavelengths 590 nm (emission) using the SPECTRAMAX® M5 instrument from Molecular Devices. Blank fluorescent reading was subtracted from all fluorescent measurement readings. Percent enzymatic remaining activity was calculated by the following equation: [(Test inhibitor fluorescent reading)/(Positive control fluorescence reading)×100%]. Percent LSD1 inhibition was calculated by following the equation: [% ILSD1 inhibition=100%−LSD1 enzymatic activity remaining].

In order to determine the $IC_{50}$ value, varying concentrations of 9 were preincubated for 5 min at room temperature prior to initiation of the reaction via the methylated peptide substrate addition. $IC_{50}$ was calculated based on nonlinear regression analysis of percent LSD1 inhibition data collected from triplicate using GraphPad PRISM® 5 software (GraphPad, San Diego, Calif.).

TABLE 5

Statistics involved in calculation of the % LSD1 inhibition of cyclic and linear peptides.

|  | (8) | (9) | (10) | (11) | (12) | (13) | (14) |
|---|---|---|---|---|---|---|---|
| Number of values | 3 | 3 | 3 | 3 | 3 | 3 | 3 |
| Minimum | 91.60 | 90.65 | 32.20 | 93.24 | 25.59 | 47.87 | 28.48 |
| 25% Percentile | 91.60 | 90.65 | 32.20 | 93.24 | 25.59 | 47.87 | 28.48 |
| Median | 97.90 | 90.88 | 38.61 | 94.04 | 30.89 | 49.14 | 32.31 |
| 75% Percentile | 100.0 | 90.99 | 45.54 | 94.16 | 86.26 | 49.78 | 67.86 |
| Maximum | 100.0 | 90.99 | 45.54 | 94.16 | 86.26 | 49.78 | 67.86 |
| Mean | 96.50 | 90384 | 38.78 | 93.81 | 47.58 | 48.93 | 42.88 |
| Std. Dev. | 4.372 | 0.1735 | 6.672 | 0.5001 | 33.60 | 0.9722 | 21.72 |
| Std. Err. | 2.524 | 0.1002 | 3.852 | 0.2888 | 19.40 | 0.5613 | 12.54 |
| Lower 95% CI of mean | 85.64 | 90.41 | 22.21 | 92.57 | −35.89 | 46.52 | −11.06 |
| Upper 95% CI of mean | 107.4 | 91.27 | 55.36 | 95.06 | 131.1 | 51.34 | 96.83 |
| Sum | 289.5 | 272.5 | 116.4 | 581.4 | 142.7 | 146.8 | 128.7 |

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. Nos. 4,870,287
5,739,169
5,760,395
5,801,005
5,824,311
5,830,880
5,846,945
7,183,059
7,192,713
PCT Publication WO2010/084160
PCT Publication WO2011/035941
Arrowsmith et al., *Nature Reviews*, 11:384, 2012.
Austin-Ward and Villaseca, *Revista Medica de Chile*, 126(7): 838-845, 1998.
Barany et al., The Peptides, Analysis, Synthesis and Biology, Vol. 2, Gross and Meienhofer, Eds. Academic Press, pp. 1-284, 1980.
Barn et al., Synthesis of an array of amides by aluminum chloride assisted cleavage on resin bound esters, *Tetrahedron Letters*, 37:3213-3216, 1996.
Belinsky et al., *Cancer Res.*, 63:7089, 2003.
Bhadra et al., *Pharmazie*, 57:5-29, 2002.
Bukowski et al., *Clinical Cancer Res.*, 4(10):2337-2347, 1998.
Chang et al., An internal-coordinate Monte Carlo method for searching conformational space, *J. Am. Chem. Soc.*, 111: 4379-4386, 1989.
Christodoulides et al., *Microbiology*, 144(Pt 11)3027-3037, 1998.
Cory et al., *Cancer Commun.*, 3:207, 1991.
Culhane et al, A mechanism-based inactivator for histone demethylase LSD1, *J. Am. Chem. Soc.*, 128:4536-4537, 2006.
Culhane et al., Comparative analysis of small molecules and histone substrate analogues as LSD1 lysine demethylase inhibitors, *J. Am. Chem. Soc.*, 132:3164-3176, 2010.
Davidson et al., *J. Immunother.*, 21(5):389-398, 1998.
DeGrado and Kaiser, Solid-phase synthesis of protected peptides on a polymer bound oxime: Preparation of segments comprising the sequences of a cytotoxic 26-peptide analogue, *J. Org. Chem.*, 47:3258-3261, 1982.
Forneris et al., Human histone demethylase LSD1 reads the histone code, *J. Biol. Chem.*, 280:41360-41365, 2005.
Forneris et al., A highly specific mechanism of histone H3-K4 recognition by histone demethylase LSD1, *J. Biol. Chem.*, 2811:35289-35295, 2006.
Forneris et al., Structural basis of LSD1-CoREST selectivity in histone H3 recognition, *J. Biol. Chem.*, 282:20070-20074, 2007.
Gawande and Branco, *Green Chemistry*, 13:3355, 2011.
Hacker et al., *Cancer Chemother. Pharmacol.*, 63:45, 2008.
Hanibuchi et al., *Int. J. Cancer*, 78(4):480-485, 1998.
Harris et al., *Clin. Pharmacokinet.*, 40:539-551, 2001.
Hayami et al., Overexpression of LSD1 contributes to human carcinogenesis through chromatin regulation in various cancers, *Int. J. Cancer*, 128:574-586, 2011.

Hazeldine et al., Low molecular weight amidoximes that act as potent inhibitors of lysine-specific demethylase 1, *J. Med. Chem.*, 55:7378-7391, 2012.
Heitjan et al., *Cancer Res.*, 53:6042, 1993.
Hellstrand et al., *Acta Oncologica*, 37(4):347-353, 1998.
Hollander, *Front. Immun.*, 3:3, 2012.
Horne, *Expert Opinion on Drug Discovery*, 6:1247, 2011.
Hruby, Designing peptide receptor agonists and antagonists, *Nat. Rev. Drug Discov.*, 1:847-858, 2002.
Huang et al., Inhibition of lysine-specific demethylase 1 by polyamine analogues results in reexpression of aberrantly silenced genes, *PNA*, 104:8023-8028, 2007.
Huang et al., *Clin. Cancer Res.*, 15:7217, 2009.
Hui and Hashimoto, *Infection Immun.*, 66(11):5329-5336, 1998.
Izumiyama et al., *Oncogene*, 22:8085, 2003.
Jenuwein and Allis, Translating the histone code, *Science*, 293:1074-1080, 2001.
Kim et al., *Nature Protocols*, 6:761, 2011.
Kozlowski et al., *Biodrugs*, 15:419-429, 2001.
Kozlowski et al., *J. Control Release*, 72:217-224, 2001.
Kurnarasinghe and Woster, *ACS Med. Chem. Lett* 5:29, 2014.
Latham and Dent, Cross-regulation of histone modifications, *Nat. Struct. Mol. Biol.*, 14:1017-1024, 2007.
Lee et al., *Lamgmuir*, 15:5500, 1999.
Leggio et al., *The Journal of Organic Chemistry*, 75:1386, 2010.
Lim et al., Lysine-specific demethylase 1 (LSD1) is highly expressed in ER-negative breast cancers and a biomarker predicting aggressive biology, *Carcinogenesis*, 31:512-520, 2010.
Merrifield, Solid phase synthesis (Nobel lecture), *Angew Chem.*, 24:799-810, 1985.
Metzger et al., *Nature*, 437:436, 2005.
Ogasawara et al., *Angew Chem. Int. Ed. Engl.*, 52:8620, 2013.
Olivos et al., *Organic Letters*, 4:4057, 2002.
Olsen, *Chembiochem.*, 11:1152, 2010.
Qin et al., *Proc. Natl. Acad. Set. USA*, 95(24):14411-14416, 1998.
Radisky et al., *J. Cell Biochem.*, 1.01:830, 2007.
Radisky and Radisky, *Reviews in Endocrine & Metabolic Disorders*, 8:279, 2007.
Reddy, *Ann. Pharmacother.*, 34:915-923, 2001.
Roberts et al., *Adv. Drug Deliv. Rev.*, 54:459-476, 2002.
Rotili and Mai, Targeting Histone Demethylases: A New Avenue for the Fight against Cancer, *Genes Cancer*, 2:663-679, 2011.
Rybinski et al., *Physiological Genomics*, 46:223-244, 2014.
Saunders et al., Conformations of Cycloheptadecane: A Comparison of Methods for Conformational Searching, *J. Am. Chem. Soc.*, 112:1419-1427, 1990.
Schafmeister et al., *J. Am. Chem. Soc.*, 122:5891, 2000.
Schmitt et al., *J. Med. Chem.*, 56:7334, 2013.
Schulte et al., Lysine-specific demethylase 1 is strongly expressed in poorly differentiated neuroblastoma: implications for therapy, *Cancer Res.*, 69:2065-2071, 2009.
Seebach et al., *Chemistry & Diodiversity*, 1:1111, 2004.
Sharma et al., (Bis)urea and (bis)thiourea inhibitors of lysine-specific demethylase 1 as epigenetic modulators, *J. Med. Chem.*, 53:5197-5212, 2010.
Sharma et al., Polyamine-based small molecule epigenetic modulators, *Med. Chem. Comm.*, 3:14-21, 2010.
Shi et al., Histone demethylation mediated by the nuclear amine oxidase homolog LSD1, *Cell*, 119:941-953, 2004.
Histone lysine demethylases: emerging roles in development, physiology and disease, *Nat. Rev. Genet.*, 8:829-833, 2007.
Shim et al., *Chem. Biol. Drug Des.*, 82:635, 2013.
Stavropoulos and Hoelz, Lysine-specific demethylase 1 as a potential therapeutic target, *Expert Opin. Ther. Targets*, 11:809-820, 2007.
Strahl and Allis, The language of covalent histone modifications, *Nature*, 403:41-45, 2000.
Suzuki and Miyata, *Journal of Medicinal Chemistry*, 54:8236, 2011.
Szeewczuk et al., Mechanistic analysis of a suicide inactivator of histone demethylase LSD1, *Biochemistry*, 46:6892-6902, 2007,
Verdine and Hilinski, *Methods Enzymol.*, 503:3, 2012.
Veronese, *Biomaterials*, 22:405-417, 2001.
Yamamoto et al., *J. Bioorg. Med. Chem.*, 17:7337, 2009.
Yang et al., Structural basis of histone demethylation by LSD1 revealed by suicide inactivation, *Nat. Struct. Mol. Biol.*, 14:535-539, 2007.
Young-Woo et al., Synthesis of all-hydrocarbon stapled a-helical peptides by ring-closing olefin methathesis, *Nature Protocols*, 6:761-771, 2011.
Zhang and Bulaj, *Curr. Med. Chem.*, 119:1602, 2012.
Zhang et al., Antiviral activity of a-helical stapled peptides designed from the HIV-1 capsid dimerization domain, *Retrovirology*, 8:28, 20111.
Zheng et al., *J. Med. Chem.*, 2013.
Zhou et al. A stable nonfluorescent derivative of resorufin for the fluorometric determination of trace hydrogen peroxide: applications in detecting the activity of phagocyte NADPH oxidase and other oxidases, *Anal. Biochem.*, 253:162-168, 1997.

What is claimed is:

1. A cyclic peptide lysine-specific demethylase 1 inhibitor comprising the sequence of H-AX$_1$TMX$_2$TARKX$_3$TX$_4$GX$_5$APRKQLA-NH$_2$ (SEQ ID NO: 8), wherein X$_1$ is K or R; X$_2$ is Q, K, or E; X$_3$ is S or E; X$_4$ is G or E; and X$_5$ is K or E, and wherein:

X$_1$ is K, X$_2$ is Q, X$_3$ is S, X$_4$ is G, and X$_5$ is E, and wherein a lactam bridge is present between X$_1$ and X$_5$;

X$_1$ is K, X$_2$ is Q, X$_3$ is E, X$_4$ is G, and X$_5$ is K, and wherein a lactam bridge is present between X$_1$ and X$_3$;

X$_1$ is K, X$_2$ is Q, X$_3$ is S, X$_4$ is E, and X$_5$ is K, and wherein a lactam bridge is present between X$_1$ and X$_4$;

X$_1$ is K, X$_2$ is E, X$_3$ is S, X$_4$ is G, and X$_5$ is K, and wherein a lactam bridge is present between X$_1$ and X$_2$;

X$_1$ is R, X$_2$ is K, X$_3$ is E, X$_4$ is G, and X$_5$ is K, and wherein a lactam bridge is present between X$_2$ and X$_3$; or X$_1$ is R, X$_2$ is Q, X$_3$ is S, X$_4$ is G, and X$_5$ is E, and wherein a lactam bridge is present between Lys9 and X$_5$.

2. The cyclic peptide of claim 1, wherein the peptide is lipidated.

3. The cyclic peptide of claim 1, wherein the peptide is PEG-ylated.

4. A pharmaceutical formulation comprising a cyclic peptide of claim 1 in a pharmaceutically acceptable carrier.

5. A method of treating a tumor cell or a subject having a tumor cell comprising administering to the tumor cell or the subject the formulation of claim 4, wherein the subject has been identified as having a lysine-specific demethylase 1 (LSD1)-overexpressing tumor.

6. A cyclic peptide lysine-specific demethylase 1 inhibitor comprising:
   (i) a peptide sequence of SEQ ID NO: 2, and wherein the lactam bridge is between Lys2 and Glu14;
   (ii) a peptide sequence of SEQ ID NO: 3, and wherein the lactam bridge is between Lys5 and Glu10;
   (iii) a peptide sequence of SEQ ID NO: 4, and wherein the lactam bridge is between Lys2 and Glu10;
   (iv) a peptide sequence of SEQ ID NO: 5, and wherein the lactam bridge is between Lys2 and Glu12; or
   (v) a peptide sequence of SEQ ID NO: 7, and wherein the lactam bridge is between Lys9 and Glu14.

7. The cyclic peptide of claim 6, wherein the peptide is lipidated.

8. The cyclic peptide of claim 6, wherein the peptide is PEG-ylated.

9. A pharmaceutical formulation comprising a cyclic peptide of claim 6 in a pharmaceutically acceptable carrier.

10. A method of treating a tumor cell or a subject having a tumor cell comprising administering to the tumor cell or the subject the formulation of claim 9, wherein the subject has been identified as having a lysine-specific demethylase 1(LSD1)-overexpressing tumor.

* * * * *